United States Patent
Jossart et al.

(10) Patent No.: US 8,812,070 B2
(45) Date of Patent: Aug. 19, 2014

(54) PORTABLE STO$_2$ SPECTROMETER

(75) Inventors: Paul J. Jossart, Hutchinson, MN (US); Michael D. Maher, Hutchinson, MN (US); Bryan J. Scheele, Hutchinson, MN (US); Roger W. Schmitz, Hutchinson, MN (US); Bradley L. Trettin, Buffalo Lake, MN (US); Daniel M. Gelfman, Minneapolis, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 1017 days.

(21) Appl. No.: 12/704,798

(22) Filed: Feb. 12, 2010

(65) Prior Publication Data

US 2010/0210929 A1    Aug. 19, 2010

Related U.S. Application Data

(60) Provisional application No. 61/152,454, filed on Feb. 13, 2009, provisional application No. 61/297,370, filed on Jan. 22, 2010.

(51) Int. Cl.
*A61B 5/00* (2006.01)

(52) U.S. Cl.
USPC ............................. 600/323; 600/310

(58) Field of Classification Search
USPC ................................. 600/310, 323
See application file for complete search history.

(56) References Cited

U.S. PATENT DOCUMENTS

| | | | |
|---|---|---|---|
| 5,279,295 A | 1/1994 | Martens et al. | |
| 5,437,275 A | 8/1995 | Amundsen et al. | |
| 5,611,337 A | 3/1997 | Bukta | |
| 5,625,931 A | 5/1997 | Visser et al. | |
| 5,676,139 A | 10/1997 | Goldberger et al. | |
| 5,817,010 A | 10/1998 | Hibl | |
| 5,879,294 A | 3/1999 | Anderson et al. | |
| 6,285,895 B1 | 9/2001 | Ristolainen et al. | |
| 6,377,840 B1 | 4/2002 | Gritsenko et al. | |
| 6,473,632 B1 | 10/2002 | Myers | |
| 6,839,583 B1 | 1/2005 | Lewandowski et al. | |
| 6,850,788 B2 * | 2/2005 | Al-Ali | 600/323 |

(Continued)

FOREIGN PATENT DOCUMENTS

| | | |
|---|---|---|
| DE | 197 14 243 A1 | 10/1998 |
| EP | 0 568 380 | 11/1993 |
| WO | WO 2006/036911 | 4/2006 |

OTHER PUBLICATIONS

International Search Report and Written Opinion issued in PCT/US2010/024017, mailed Jun. 10, 2010, 14 pages.

*Primary Examiner* — Clayton E LaBalle
*Assistant Examiner* — Warren K Fenwick
(74) *Attorney, Agent, or Firm* — Faegre Baker Daniels LLP

(57) ABSTRACT

Devices, systems, and methods for measuring tissue oxygen saturation (StO$_2$) within the body are disclosed. A patient interface for use with a tissue measurement instrument can include a spring clip having a first arm and a second arm, a spring configured to bias the first and second arms together, and a means for optically connecting the patient interface to the tissue measurement instrument. The patient interface can be used in conjunction with an optical sourcing and receiving unit of a monitor for measuring tissue oxygen saturation at a measurement site on the patient. A testing interface on an external portion of the instrument housing and a testing module can be used to perform tests on the instrument.

24 Claims, 32 Drawing Sheets

(56) References Cited

U.S. PATENT DOCUMENTS

| | | |
|---|---|---|
| 7,047,054 B2 | 5/2006 | Benni |
| 7,165,893 B2 | 1/2007 | Schmitz |
| 7,254,434 B2 * | 8/2007 | Schulz et al. .................. 600/344 |
| 7,280,858 B2 * | 10/2007 | Al-Ali et al. .................. 600/323 |
| 7,311,686 B1 | 12/2007 | Iglesias et al. |
| 7,328,052 B2 | 2/2008 | Samsoondar et al. |
| 7,460,897 B1 | 12/2008 | Flessland et al. |
| 7,574,244 B2 | 8/2009 | Eghbal et al. |
| 2003/0144608 A1 | 7/2003 | Kojima et al. |
| 2005/0167806 A1 | 8/2005 | Mullen et al. |
| 2005/0228248 A1 * | 10/2005 | Dietiker ........................ 600/323 |
| 2005/0277818 A1 | 12/2005 | Myers |
| 2006/0211924 A1 * | 9/2006 | Dalke et al. .................... 600/310 |
| 2006/0224058 A1 * | 10/2006 | Mannheimer ................. 600/323 |
| 2007/0032712 A1 * | 2/2007 | Raridan et al. ............... 600/323 |
| 2007/0078316 A1 * | 4/2007 | Hoarau et al. ................ 600/323 |
| 2007/0078317 A1 * | 4/2007 | Matlock ........................ 600/323 |
| 2007/0156037 A1 | 7/2007 | Pilon et al. |
| 2008/0300474 A1 | 12/2008 | Benni et al. |
| 2009/0043180 A1 | 2/2009 | Tschautscher et al. |
| 2010/0004518 A1 * | 1/2010 | Vo et al. ........................ 600/310 |

* cited by examiner

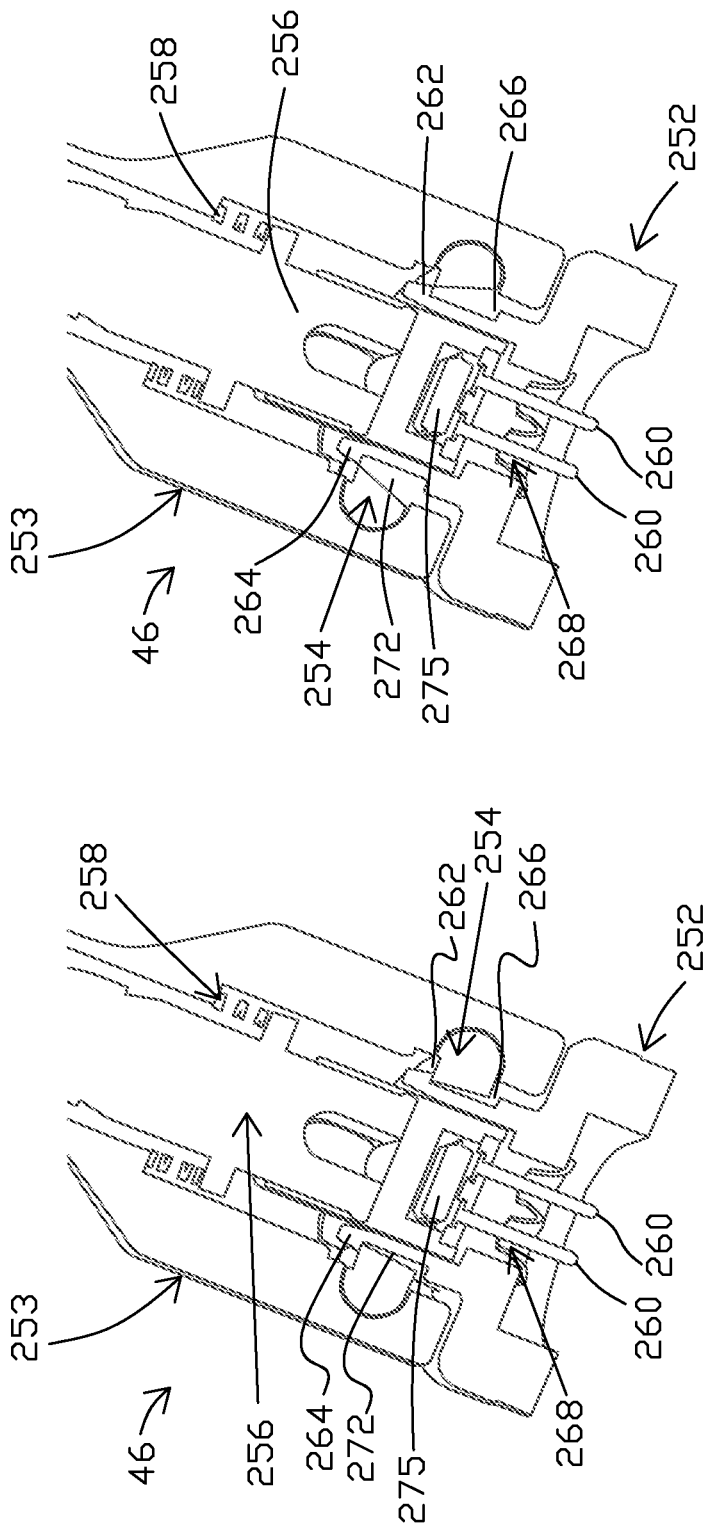

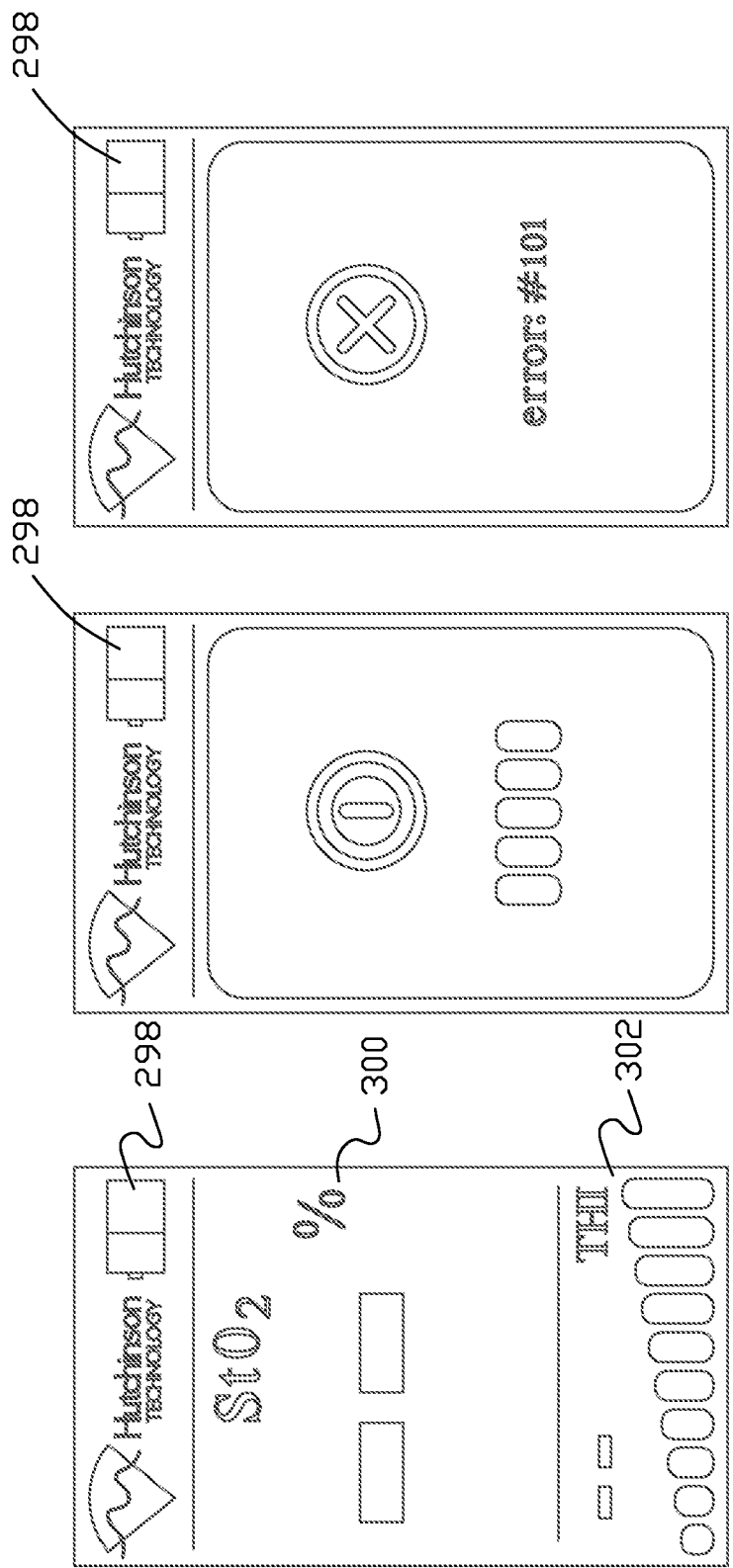

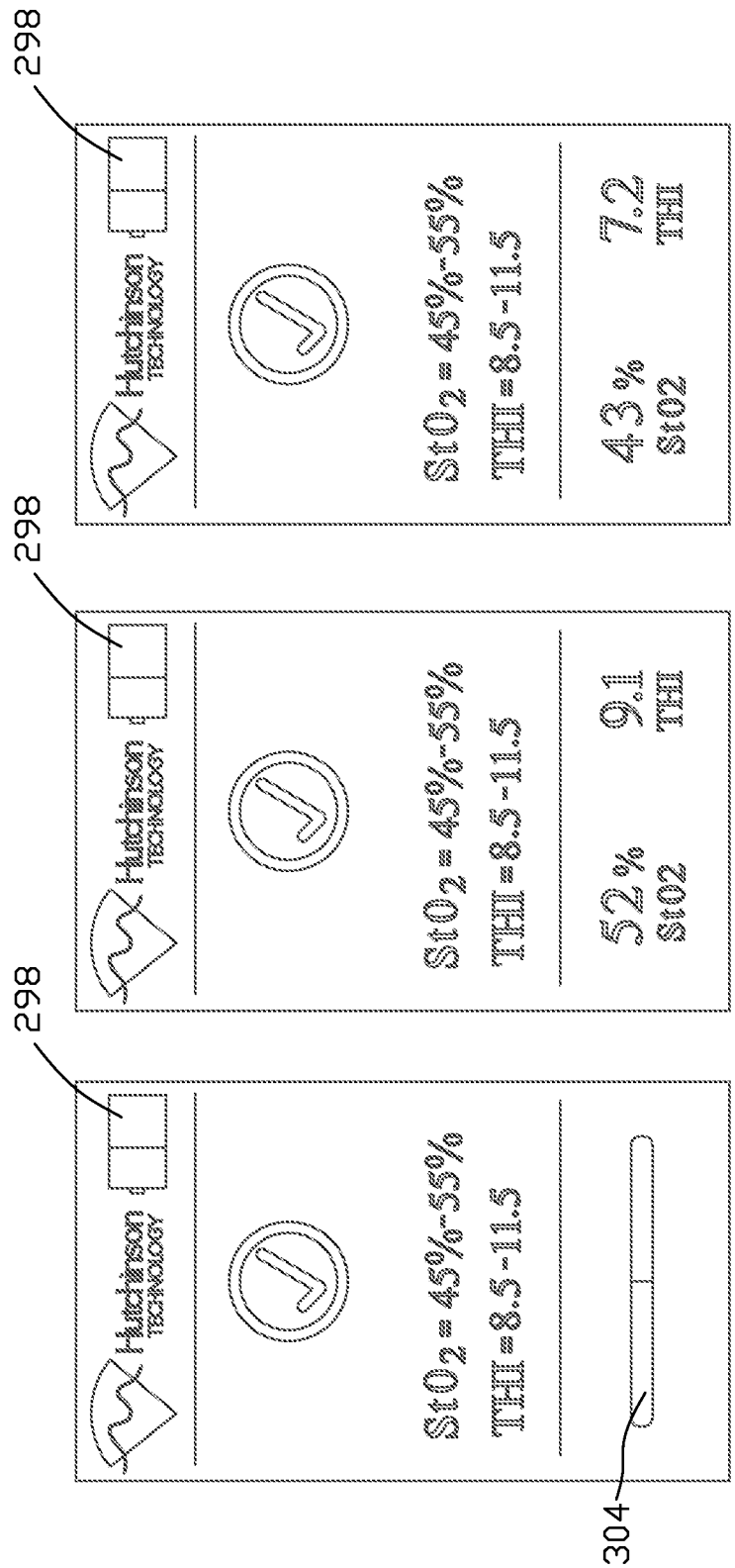

PORTABLE STO$_2$ SPECTROMETER

CROSS-REFERENCE TO RELATED APPLICATIONS

This application claims benefit under 35 U.S.C. §119 to U.S. Provisional Application No. 61/152,454, filed Feb. 13, 2009, entitled "Handheld StO2 Spectrometer," and to U.S. Provisional Application No. 61/297,370, filed Jan. 22, 2010, entitled "Portable StO2 Spectrometer," both of which are incorporated herein by reference in their entirety for all purposes.

TECHNICAL FIELD

The present invention relates to spectrometers for measuring one or more parameters within the body. More specifically, the present invention relates to near infrared (NIR) spectrometers for measuring tissue oxygen saturation (StO$_2$).

BACKGROUND

Overcrowding in hospital emergency departments is a world-wide crisis resulting in long wait times and detriments to patient safety. Tissue oxygen saturation (StO$_2$) is sometimes an early indicator of perfusion status in patients experiencing undifferentiated shock in emergency room triage settings. By indicating the need for, and allowing the start of, fluid and antibiotic therapy, monitoring StO$_2$ in an emergency room triage setting can help identify high-risk patients in need of immediate attention and focus scarce emergency room resources on the most critical patients. High-risk patients who receive immediate StO$_2$ monitoring in an emergency room setting have been shown to receive effective interventions sooner, resulting in significant reductions in ICU admission, length of stay, morbidity, and mortality.

Near infrared (NIR) spectrometer systems for measuring tissue oxygen saturation (StO$_2$) are known and disclosed in, for example, U.S. Pat. No. 7,947,054 to Benni and U.S. Pat. No. 6,377,840 to Gritsenko et al., each of which are incorporated herein by reference in their entirety for all purposes.

The Benni patent discloses a spectrometer utilizing four laser diodes to provide discreet measurement radiation within the 700 nm to 1000 nm wavelength range. The use of laser diodes as the radiation source requires relatively complicated power controls and safety interlock controls. Coupled to each laser diode is a multimode optical fiber having a core diameter of 200 μm. A dual ball lens optical coupler assembly couples the fibers from each laser diode to a single multimode fiber having a core diameter of 300 μm, which connects to the patient interface. The patient interface is designed to be reused multiple times and includes a prism assembly to direct measurement radiation to the patient's measurement site and an EMI shielded photodiode assembly for receiving reflected radiation from the measurement site. A shielded electrical cable interconnects the photodiode assembly to the spectrometer's system processor. Frequent handling, detachment and reattachment of the patient interface subjects the single multimode 300 μm diameter fiber to multiple bending stresses, which can lead to premature failure of the fiber. Additionally, manufacturing the patient interface is made more complex and is thus more costly since the prism and EMI shielded photodiode assemblies are incorporated into the patient interface.

The Gritsenko et al. patent discloses a spectrometer utilizing four LED's to provide discreet measurement radiation at wavelengths of 680 nm, 720 nm, 760 nm and 800 nm, respectively. The spectrometer includes an electronics package, an optical probe for interfacing with the patient measurement site, and a probe connector for coupling the optical probe to the electronics package. The electronics package includes a processor/controller and a relatively complex optical bench for detecting and processing radiation that has been reflected from the measurement site. The optical probe connector includes the measurement source and reference LED's, an electrical connector for connecting the LED's to the electronics package, optical fibers for transmitting measurement and reflected radiation to and from the optical probe, and optical connector ferrules for connecting reference and reflected radiation to the optical bench. The optical bench comprises a series of mirrors, band pass filters, and photomultiplier tube sensors. In operation, measurement radiation from the 680 nm, 720 nm, 760 nm, and 800 nm LED's is transmitted simultaneously to the tissue within the measurement site. Radiation reflected from the measurement site is transmitted to the optical bench via the optical probe connector where it is separated into discreet wavelength components. The optical probe that interfaces with the patient measurement site is connected to the optical probe connector by an optical fiber bundle comprising a single fiber for each of the measurement radiation LED's and a single fiber for transmitting reflected radiation.

There remains a need for a portable, hand-held spectrometer for quickly and efficiently measuring tissue oxygenation. To be commercially viable, any such spectrometer must be easy to use, easy to maintain, and cost effective to manufacture.

SUMMARY

The present invention relates to devices, systems, and methods for measuring tissue oxygen saturation (StO$_2$). An illustrative system for measuring tissue oxygen saturation includes a patient interface configured for transmitting measurement radiation to a measurement site and receiving reflected radiation from the measurement site, an optical sourcing and receiving unit, an optical signal converter configured for converting reflected radiation into a digital electrical signal, and a processor configured for converting the digital electrical signal into at least one parameter related to tissue oxygenation. In some embodiments, the optical sourcing and receiving unit includes a number of light sources each configured to transmit near infrared light at a different wavelength, a mixer bar, a fiber optic fountain including a number of fiber optic bundles in optical communication with the light sources and mixer bar, and conditioning optics configured to direct radiation from each light source onto a corresponding fiber optic bundle.

A patient interface for use with a tissue measurement instrument in accordance with an illustrative embodiment includes a spring clip including a first arm member and a second arm member, a spring configured to bias the first and second arm members together, and a means for optically connecting the patient interface to the tissue measurement instrument. The first and second arm members are configured to provide a clamping force to the patient to secure the interface firmly against a measurement site such as on the thenar eminence on the patient's hand. In some embodiments, the spring comprises a low spring rate spring configured to provide a constant or near constant pressure application to the patient over a dynamic range of hand sizes. A number of ports on one or both of the arm members are used for transmitting and receiving light. In some embodiments, the spring includes a number of bending spring elements that increase the effective chord length of the spring. A light shield can be used to prevent undesired light from interfering with the measurement light entering and the reflected light exiting the patient's body via the radiation ports.

A tissue measurement instrument in accordance with an exemplary embodiment includes a testing interface that can be used to test, and in some cases further calibrate, the instrument. The tissue measurement instrument includes a housing including an external clip area configured to receive a patient interface during those periods when the patient interface is not in use. A number of optical ports on the housing are configured to optically communicate with the radiation ports on the patient interface. A test module disposed within an interior of the housing and in optical communication with the optical ports is configured to perform a self-check on the instrument.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 24 is a cross-sectional view of the electro-optical sensor connector of FIG. 23 with the push button shown in an engaged position;

FIG. 25 is a cross-sectional view of the electro-optical sensor connector of FIG. 23 with the push button shown in a disengaged position;

FIGS. 31A-31J are several screen-shots showing an illustrative graphical user interface (GUI) that can be displayed on a portable, hand-held $StO_2$ monitor in accordance with an illustrative embodiment.

Figure 1:
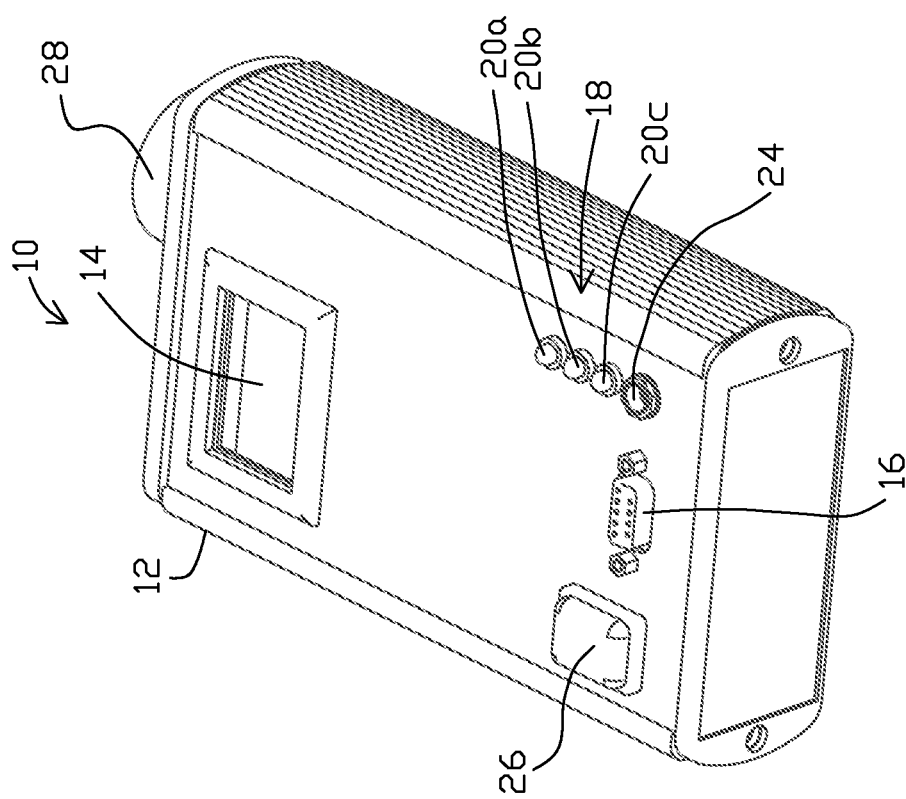
FIG. 1 is a perspective view of a portable, hand-held $StO_2$ monitor in accordance with an illustrative embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of a portable, hand-held tissue oxygen saturation ($StO_2$) monitor 10 in accordance with an illustrative embodiment. As shown in FIG. 1, the $StO_2$ monitor 10 includes a housing 12 sized and shaped to be easily held in a physician's, nurse's, or other user's hand. The housing 12 may include finger grips and/or a rubberized coating to facilitate gripping by the user's hand. The housing 12 may also include a clip to facilitate attachment of the monitor 10 to a belt or pocket.

A digital display 14 on the housing 12 is configured to display a patient's $StO_2$ values as well as other status information. In some embodiments, the display 14 comprises a graphical user interface (GUI) configured to display the patient's current and/or one or more previous $StO_2$ values, an averaged $StO_2$ value taken over time, the patient's tissue hemoglobin index (THI), the operational status of the monitor 10, the battery status of the monitor 10, as well as other information relating to the monitor 10 and/or the health of the patient. Several illustrative display screens that can be provided as part of a GUI are disclosed further herein with respect to FIGS. 31A-31J.

An interface 16 on the housing 12 is configured to permit the monitor 10 to be connected to one or more other devices to transmit and/or receive information to and from the monitor 10. In some embodiments, the interface 16 comprises a PC computer connection for interfacing with a computer or computer network to capture historical $StO_2$ data and/or to download a live $StO_2$ data stream. In some embodiments, the interface 16 comprises a wireless interface for wirelessly communicating with another device. Other information such as a time/date stamp can be transmitted along with each sensed $StO_2$ measurement to permit further analysis of the data. In some embodiments, the interface 16 may further facilitate programming updates or permit the uploading of data to the monitor 10, if desired.

A battery indicator 18 provides an indication of the battery life of the monitor 10. In one embodiment, and as shown in FIG. 1, the battery indicator 18 comprises a 3-LED battery-life indicator 18 in which a first, green LED 20a indicates more than 75% battery life, a second, yellow LED 20b indicates between 50% and 75% battery life, and a third, red LED 20c indicates less than 50% battery life. An AC power port 24 can be used to provide power to the monitor 10 and/or to recharge a rechargeable battery or power source within the monitor 10. An on/off switch 26, in turn, is used to turn the monitor 10 on and off.

In some embodiments, and as further shown in FIG. 1, the monitor 10 includes a sensor connector 28 for releasably connecting an $StO_2$ sensor patient interface to the housing 12, as discussed further herein. In one embodiment, for example, the sensor connector 28 can be used to interchangeably connect any of the various sensor patient interfaces discussed herein with respect to FIGS. 8-22 to the monitor 10. In some embodiments, the sensor connector 28 can comprise a releasable connector such as connector 46 discussed herein with respect to FIGS. 23-27. In other embodiments, the sensor patient interface can be incorporated directly into the housing 12 of the monitor 10, or can comprise a separate unit that is fixedly secured to the housing 12. Another example of a sensor connector is disclosed in U.S. Pat. No. 7,165,893 to Schmitz, which is incorporated herein by reference in its entirety for all purposes.

In use, the monitor 10 can be used to provide continuous or spot-check monitoring of a patient in real-time. $StO_2$ measurements sensed by the monitor 10 as well as other useful information can be provided on the display 14 and/or transmitted to another device for further analysis. In some embodiments, for example, the $StO_2$ measurements taken by the monitor 10 can be continuously displayed on the display 14 while also being transmitted to another device such as an electrocardiogram (ECG) monitor for analysis along with other information such as ECG or heart rate data. The monitor 10 enables an immediate indication of a patient's tissue perfusion status. Spot-checking tissue perfusion on a number of patients in a triage setting provides for the efficient and timely treatment of those patients at highest risk. The portability of the monitor 10 allows multiple physicians, nurses, or other users within an institution to be equipped with the means to readily and efficiently monitor patient perfusion status, resulting in a lower per-use cost. In addition, the monitor 10 is smaller and lighter than conventional $StO_2$ monitors, and is readily usable in confined spaces such as ambulances, helicopters, emergency medicine, and critical care environments.

Figure 2:
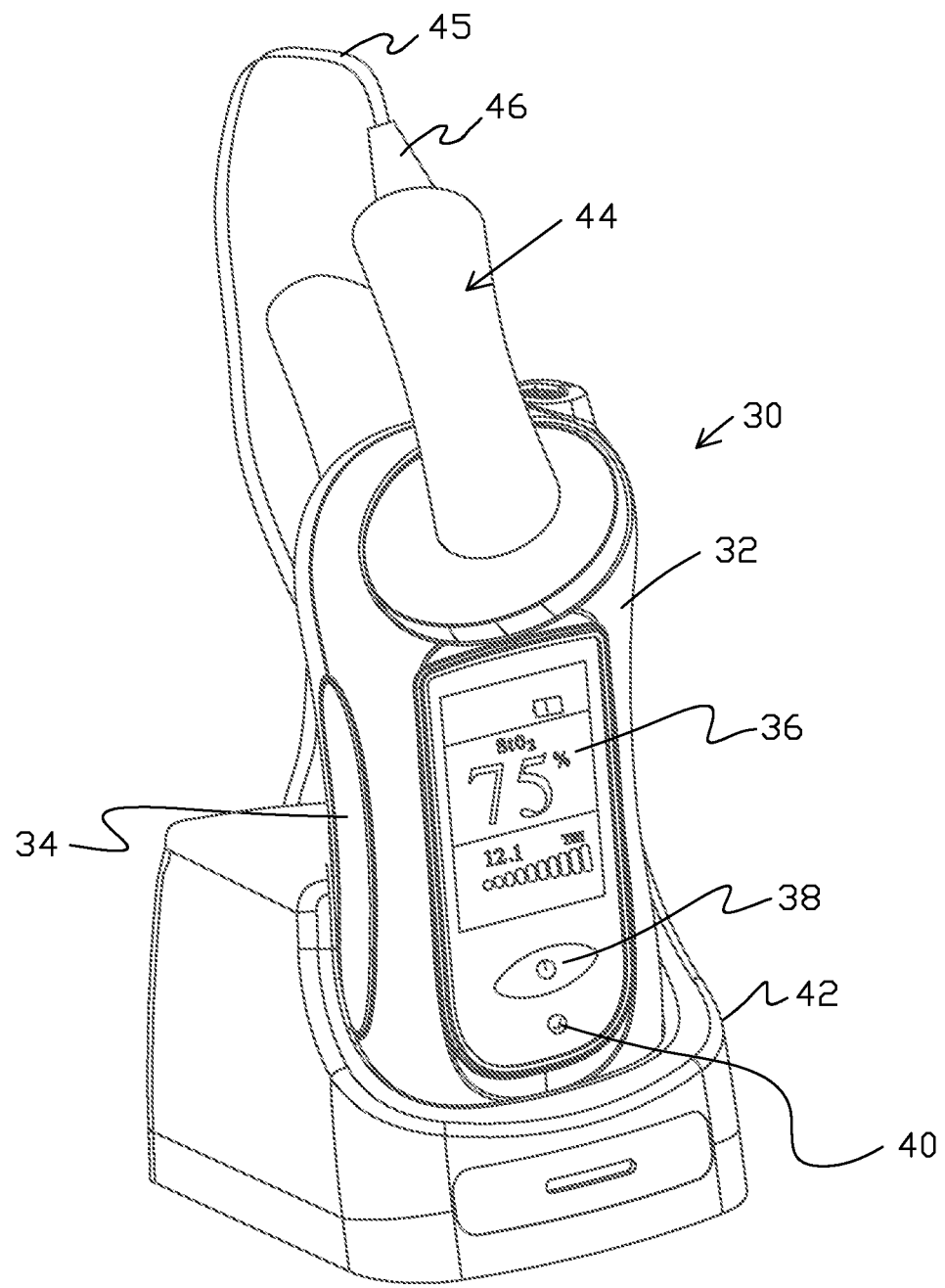
FIG. 2 is a perspective view of a portable, hand-held $StO_2$ monitor in accordance with another illustrative embodiment adapted to couple to a base unit.

FIG. 2 is a perspective view of a portable, hand-held $StO_2$ monitor 30 in accordance with another illustrative embodiment adapted to couple to a base unit. As shown in FIG. 2, the $StO_2$ monitor 30 includes a housing 32 sized and shaped to be easily held in a physician's, nurse's, or other user's hand. The housing 32 may include finger grips 34 and/or a rubberized coating to facilitate gripping by the user's hand. The housing 32 may further include a clip to facilitate attachment of the monitor 30 to a belt or pocket. A digital display 36 on the housing 32 is configured to display a patient's $StO_2$ values as well as other status information. In some embodiments, the display 36 comprises a graphical user interface (GUI) that displays the patient's current and/or one or more previous $StO_2$ values, the patient's tissue hemoglobin index (THI), the operational status of the monitor 30, the battery status of the monitor 30, as well as other information relating to the monitor 30 and/or health of the patient. Other features such as an on/off switch 38 and a system check button 40 can be provided on the housing 32, as shown.

The monitor 30 can be releasably secured to a base unit 42 that can be used to recharge the monitor 30 during periods of nonuse, and in some embodiments, permits real-time and/or stored $StO_2$ measurements to be transmitted to another device via either a wired or wireless connection. In some embodiments, for example, the act of connecting the monitor 30 to the base unit 42 automatically prompts the monitor 30 to transmit current and/or stored $StO_2$ data to another device for further analysis. In other embodiments, the monitor 30 can be equipped with an interface (e.g., interface 16) to facilitate connection of the monitor 30 to the base unit 42 or directly to another device.

A patient interface 44 is configured to facilitate use of the monitor 30 in an ambulatory setting or at locations where it may be difficult to connect the monitor 30 to the patient. The patient interface 44 can be coupled to the housing 32 via an optical cable 45 and electro-optical connector 46, and includes a means for transmitting and receiving near infrared (NIR) light. In some embodiments, and as discussed further herein, the patient interface 44 comprises a self-adjusting clip that can be clipped onto a patient's hand or other body extremity to secure the interface 44 to the patient.

Figure 3B:
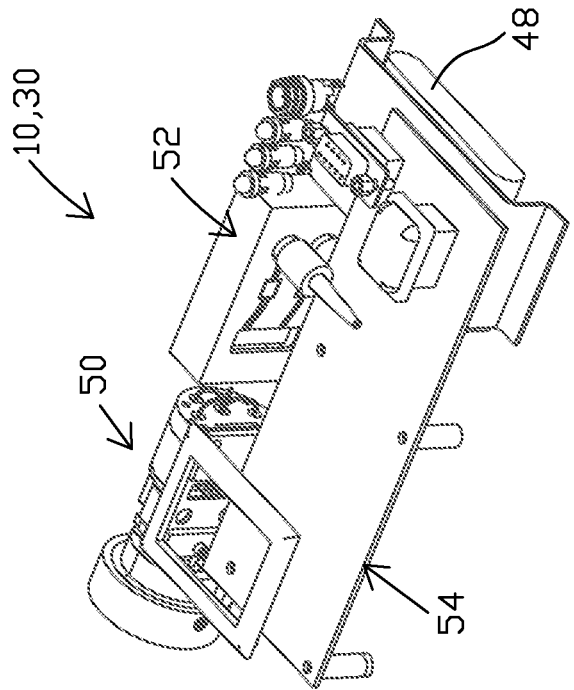
FIGS. 3A-3B are perspective views showing several internal components of a portable, hand-held $StO_2$ monitor in accordance with an illustrative embodiment.
Figure 3A:
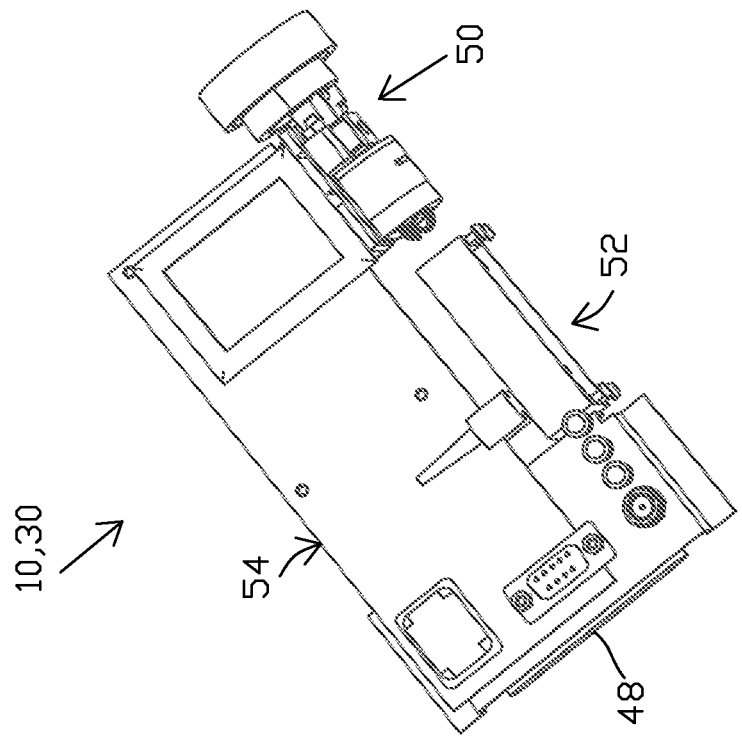

FIGS. 3A-3B are perspective views showing several example internal components of a portable, hand-held $StO_2$ monitor in accordance with an illustrative embodiment. FIGS. 3A-3B may represent, for example, several illustrative components within the monitors 10,30 described herein with respect to FIGS. 1 and 2, respectively. As shown, the monitor 10,30 can include a power supply 48 comprising, for example, four rechargeable lithium ion batteries, an optical sourcing and receiving unit 50 for sending near-infrared measurement radiation to and receiving reflected radiation back from the patient interface, and an optical signal converter 52 for converting analog feedback measurements and received reflected radiation into a digital electrical signal. A digital processing board 54 is configured for controlling the timing of several measurement radiation sources, converting the digital signals from received reflected radiation into a two-digit $StO_2$ reading, and processing the digital signals of the feedback measurement radiation to compensate for variations in measurement radiation due to degradation of the measurement radiation sources. In some embodiments, the digital electrical signals from the reflected radiation may be converted to an $StO_2$ value using an algorithm such as that disclosed in U.S. Pat. No. 5,879,294 to Anderson et al., which is incorporated herein by reference in its entirety for all purposes. Additionally, and in some embodiments, the digital signals from the reflected radiation may be converted to a tissue hemoglobin index (THI) measurement using an algorithm such as that disclosed in U.S. Pat. No. 6,473,632 to Myers, which is incorporated herein by reference in its entirety for all purposes.

Figure 4:
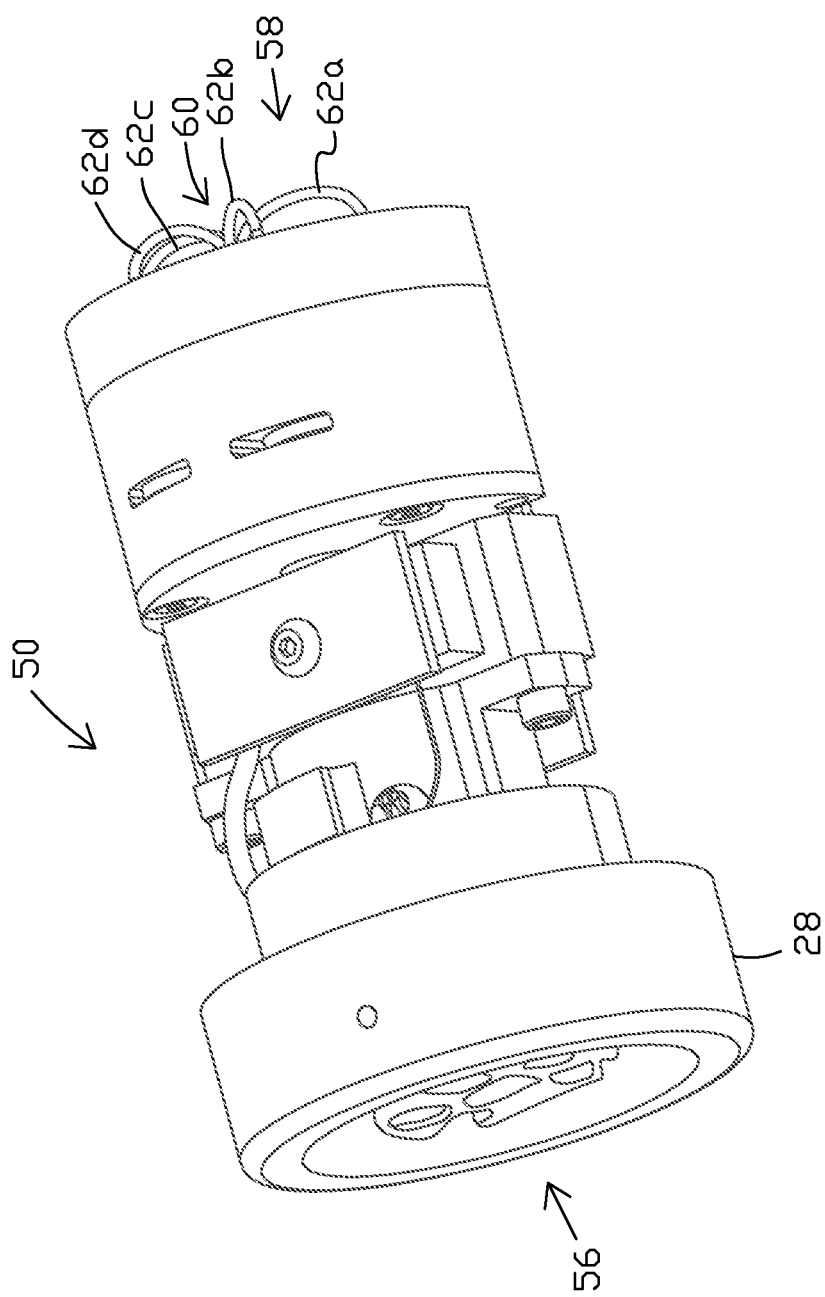
FIG. 4 is a perspective view showing the optical sourcing and receiving unit of FIG. 3 in greater detail.

FIG. 4 is a perspective view showing the optical sourcing and receiving unit 50 of FIG. 3 in greater detail. As shown in FIG. 4, the optical sourcing and receiving unit 50 includes a first end section 56 and a second end section 58. The first end section 56 of the unit 50 includes the sensor connector 28 used to couple the monitor 10 to a patient interface (not shown). The second end section 58 of the unit 50, in turn, includes a fiber optic fountain 60, which as discussed further herein, includes a number of fiber optic bundles 62a,62b,62c,62d that redirect the near infrared light waves transmitted from a number of LEDs within the unit 50 in a direction back towards the first end section 56. In use, the sensor connector 28 can be connected to a patient interface that allows spot-check monitoring and continuous, real-time monitoring of a patient's $StO_2$ levels.

Figure 5:
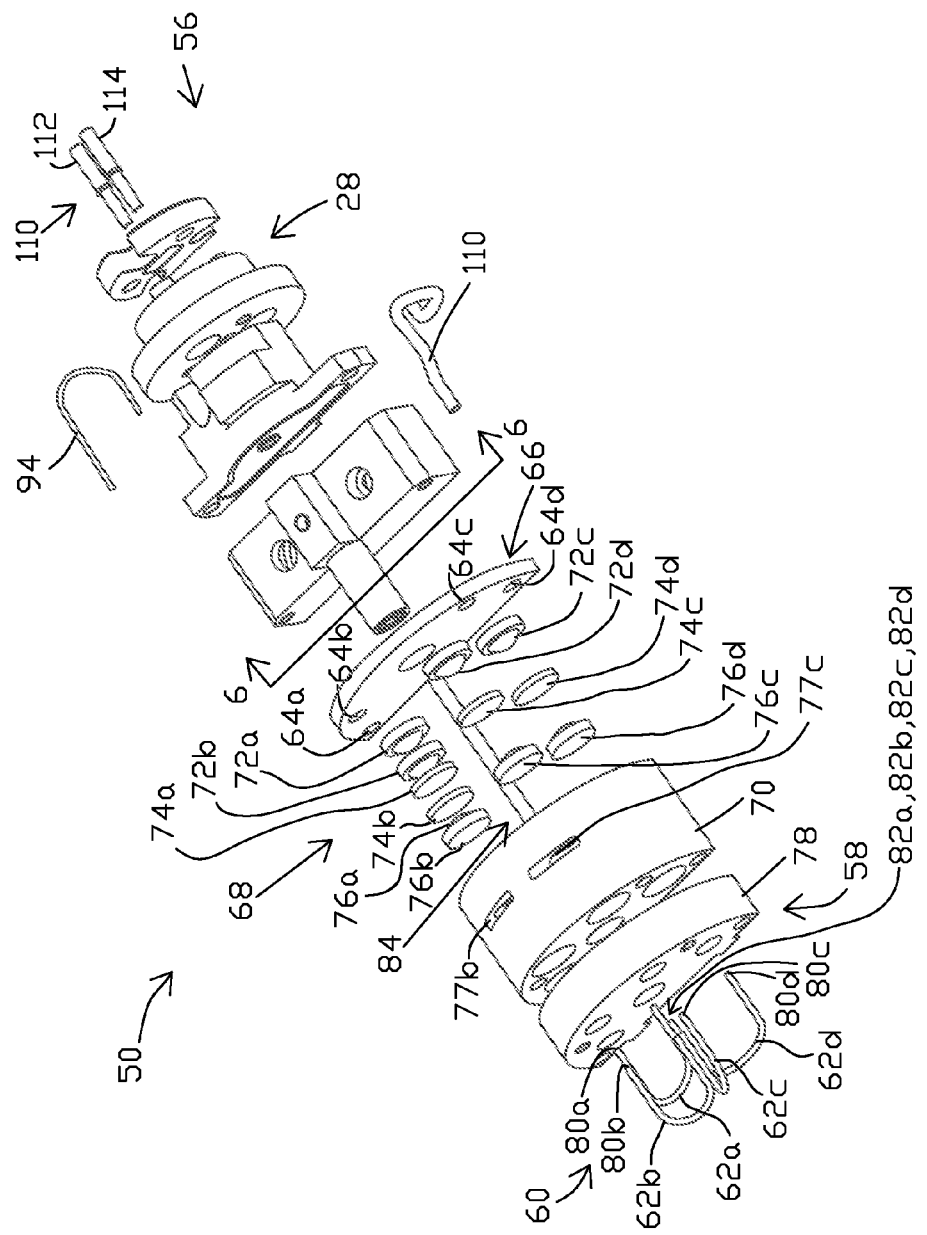
FIG. 5 is an exploded view of the optical sourcing and receiving unit of FIG. 4.

FIG. 5 is an exploded view of the optical sourcing and receiving unit 50 of FIG. 4. As further shown in FIG. 5, the unit 50 includes four LED's 64a,64b,64c,64d mounted on an LED source board 66. In one embodiment, the LED's 64a, 64b,64c,64d emit near-infrared measurement radiation generally centered at wavelengths of 680 nm, 720 nm, 760 nm and 800 nm, respectively. In other embodiments, fewer or greater wavelengths of measurement radiation may be employed such as that disclosed, for example, in U.S. Pat. No. 7,613,489 to Myers, which is incorporated herein by reference in its entirety for all purposes.

The emitted radiation from each LED 64a,64b,64c,64d passes through conditioning optics 68 to direct the radiation from each LED 64a,64b,64c,64d onto a corresponding fiber optic bundle 62a,62b,62c,62d within the fiber optic fountain 60. The conditioning optics 68, mounted in an optics housing 70, include, for each LED, a collimating lens 72a,72b,72c, 72d, a band pass filter 74a,74b,74c,74d, and a focusing lens 76a,76b,76c,76d. The band pass filters 74a,74b,74c,74d are mounted in corresponding slots 77a,77b,77c,77d (77a and 77d are hidden in FIG. 5) within the optics housing 70, and are configured to filter the emitted radiation to within +/−10 nm at full width-half max for each LED 64a,64b,64c,64d. The band pass filter slots 77a,77b,77c,77d allow the filters 74a,74b, 74c,74d to be custom matched to a given LED 64a,64b,64c, 64d in order to optimize the output signal.

The fiber optic fountain 60 is mounted on a fountain base 78, and includes four flexible fountain fiber bundles 62a,62b, 62c,62d. In one embodiment, each fountain fiber bundle 62a, 62b,62c,62d includes approximately 200 borosilicate glass fibers, each having a diameter of about 50 µm. Because bend loss is proportional to fiber diameter, the diameter of each fiber within a bundle 62a,62b,62c,62d must be small in order to achieve the tight fountain bend radii while maximizing radiation transmission. Borosilicate glass or equivalent provides a high numerical aperture required for the optical sourcing and receiving unit 50. The fiber optic fountain 60 enables a significantly smaller and more compact optical sourcing and receiving unit 50 by turning the measurement radiation, originally emitted in a direction towards the second end section 58 of the unit 50, in an opposite direction towards the first end section 56 and the sensor connector 28 of the $StO_2$ monitor 10,30.

The input end 80a,80b,80c,80d of each fountain fiber bundle 62a,62b,62c,62d is optically coupled to a corresponding LED 64a,64b,64c,64d via the conditioning optics 68. The output end 82a,82b,82c,82d of each fountain fiber bundle 62a,62b,62c,62d, in turn, is optically coupled to a square mixer bar 84. Optical coupling gel is used to reduce Fresnel reflections and eliminate thin film effects at the optical interfaces at the output ends 82a,82b,82c,82d of the fountain fiber bundles 62a,62b,62c,62d. The square mixer bar 84 is made, for example, from SF 11 glass produced by Schott North America Inc. of Duryea, Pa., and is sized and shaped to minimize the variation and equally distribute the intensity of the measurement radiation output from the optical sourcing and receiving unit 50 via the sensor connector 28. Schott SF 11 glass, or equivalent, can be used because, among other things, it does not solarize in medical x-ray environments, and it provides desirable optical (e.g., transmittance, refractive index, dispersion), mechanical and thermal properties for the range of wavelengths employed. The fiber optic fountain 60 enables the LED source board 66 to be located approximately midway along the length of the square mixer bar 84, thus providing for a longer mixer bar that allows more thorough mixing while maintaining overall compactness of the system. Straight wall guiding is required to maintain perpendicularity (parallelism to optical axis) between the conditioning optics 68 and the polished input ends 80a,80b,80c,80d of the fountain fiber bundles 62a,62b,62c,62d. Straight wall guiding is also required to maintain perpendicularity (parallelism to optical axis) between the square mixer bar 84 and the polished output ends 82a,82b,82c,82d of the fountain fiber bundles 62a,62b,62c,62d. Since the input and output ends 80a,80b, 80c,80d,82a,82b,82c,82d of the fountain fiber bundles 62a, 62b,62c,62d and thus the straight wall fiber guides lie essentially within a single plane in the fountain base 78, a shorter, more compact overall optical path is achieved.

Figure 6:
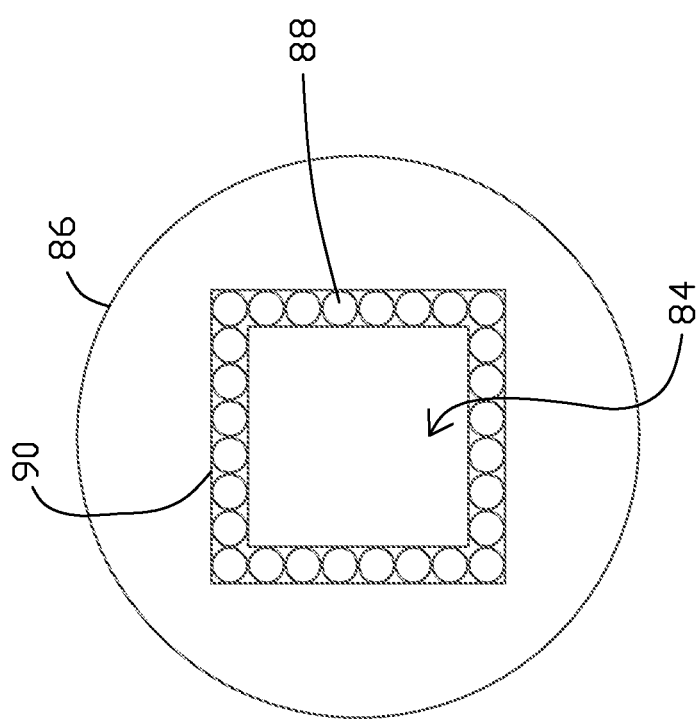
FIG. 6 is a cross-sectional view showing the square bar housing across line 6-6 in FIG. 5.

FIG. 6 is a cross-sectional view showing the square mixer bar 84 across line 6-6 in FIG. 5. As shown in FIG. 6, the square mixer bar 84 is enclosed and centered within a square bar housing 86. In some embodiments, the square bar housing 86 is made of Kovar® alloy, which has a coefficient of thermal expansion matched to the square mixer bar glass. In certain embodiments the square mixer bar 84 is mounted in the square bar housing 86 with a glass bubble-filled epoxy 88. An example epoxy is Epo-Tek® 301, produced by Epoxy Technology of Billerica, Mass., which has a lower numerical aperture than the mixer bar to maintain total internal reflection of the measurement radiation within the mixer bar 84. The glass bubbles (e.g., 3M™ iM30K Hi-Strength Glass Bubbles produced by 3M of St. Paul, Minn.) may have an average diameter of 18 µm each and provide a relatively solid, thin, uniform epoxy bond line to prevent the square mixer bar 84 from contacting the inner walls 90 of the square bar housing 86 and to reduce any mismatch and to maximize radiation transfer between the mixer 84 and adjacent optics. The thin, uniform epoxy bond line provides for a stronger, essentially tension-free, optically superior bond between the square mixer bar 84 and the housing walls 90. A thicker, non-uniform bond line would be more susceptible to failure and more shrinkage during curing. A failed bond line could cause shifting of the mixer bar off-optical axis or create air gaps resulting in undesirable Fresnel effects at the optical interfaces. Tension in the mixer bar 84 caused from increased shrinkage of a thicker bond line would also have undesirable effects on the optical throughput.

As further shown in FIGS. 4-5, the output end 92 of the square mixer bar 84 is optically coupled to a feedback fiber 94 and the sensor connector 28. The feedback fiber 94 may be made from borosilicate glass fiber having a diameter of 250 µm, and directs a portion of the measurement radiation (i.e., as feedback measurement radiation) to the optical signal converter 52 where it is converted into a digital electrical signal and used by the processing board 54 to compensate for changes in source LED 64a,64b,64c,64d intensity. Alternately, a fiber bundle may be used to direct feedback measurement radiation to the optical signal converter 52. The remainder of the measurement radiation is transmitted to the measurement site on the patient via the sensor connector 28 and patient interface, as discussed further herein.

Figure 7:
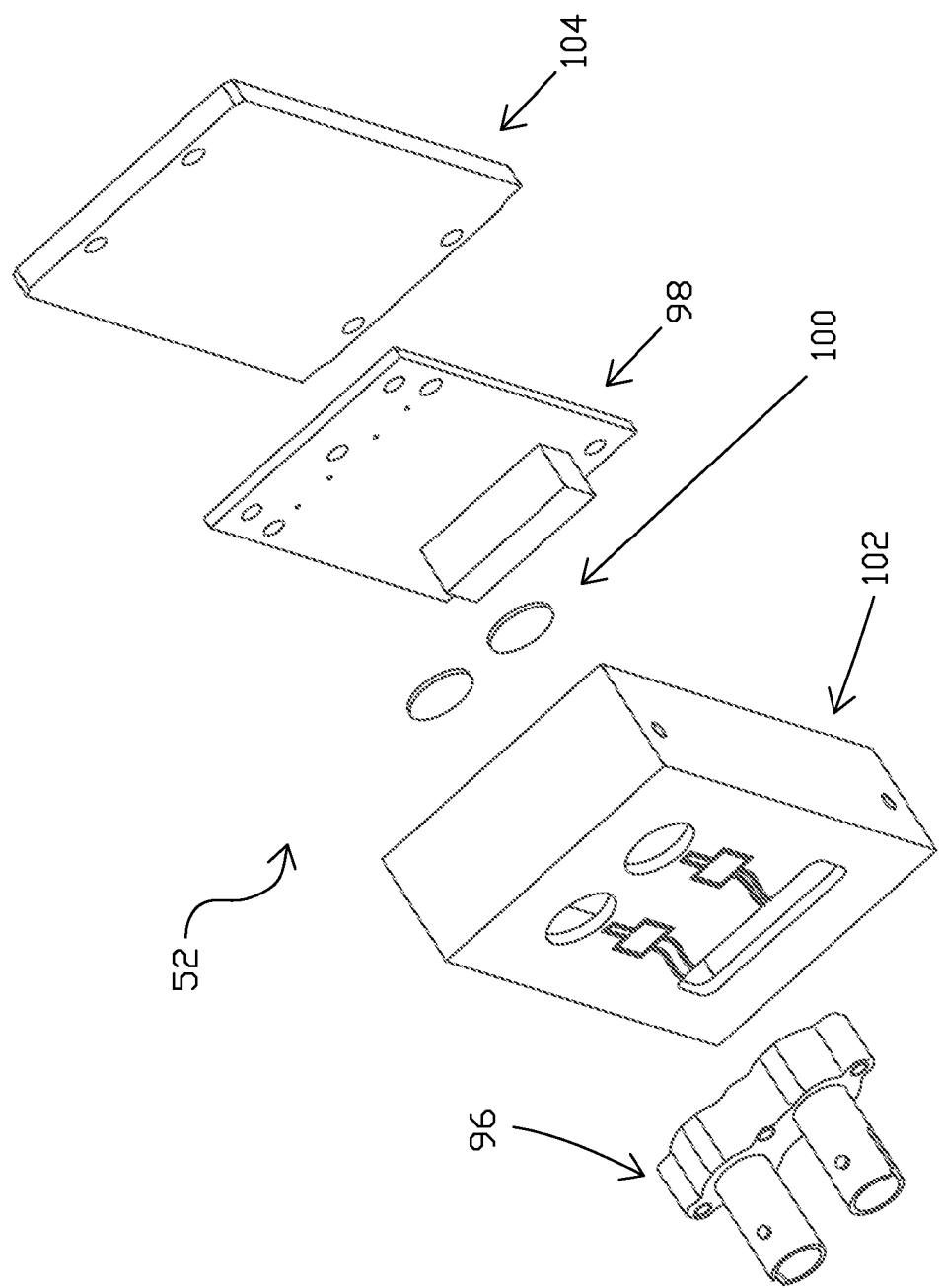
FIG. 7 is an exploded view showing an optical signal converter in accordance with an illustrative embodiment.

FIG. 7 is an exploded view showing an optical signal converter 52 in accordance with an illustrative embodiment. As shown in FIG. 7, the converter 52 includes a fiber connector/photo-diode housing 96, a circuit board 98 for converting analog radiation to digital signals, and ambient light filters 100, all of which are enclosed via a housing 102 and cover 104. In use, the ambient light filters 100 help ensure an accurate $StO_2$ measurement by preventing stray ambient light from interfering with the reflected and feedback radiation.

During operation, the LED's 64a,64b,64c,64d are sequentially energized to transmit measurement radiation from the optical sourcing and receiving unit 50, one wavelength at a time, to the measurement site. Radiation reflected from the tissue within the measurement site is transmitted back through the optics path to the digital processing board 54 via the optical signal converter 52 where an absorbance value is calculated. This send-receive absorbance calculation process is repeated for each of the four measurement radiation wavelengths. A ratioed second derivative absorbance value is calculated from the measured absorbance values and is compared with predetermined stored data correlating ratioed second derivative absorbance values with $StO_2$ values. In this manner, $StO_2$ values are calculated and displayed every two seconds, or at some other desired time period.

Figure 8:
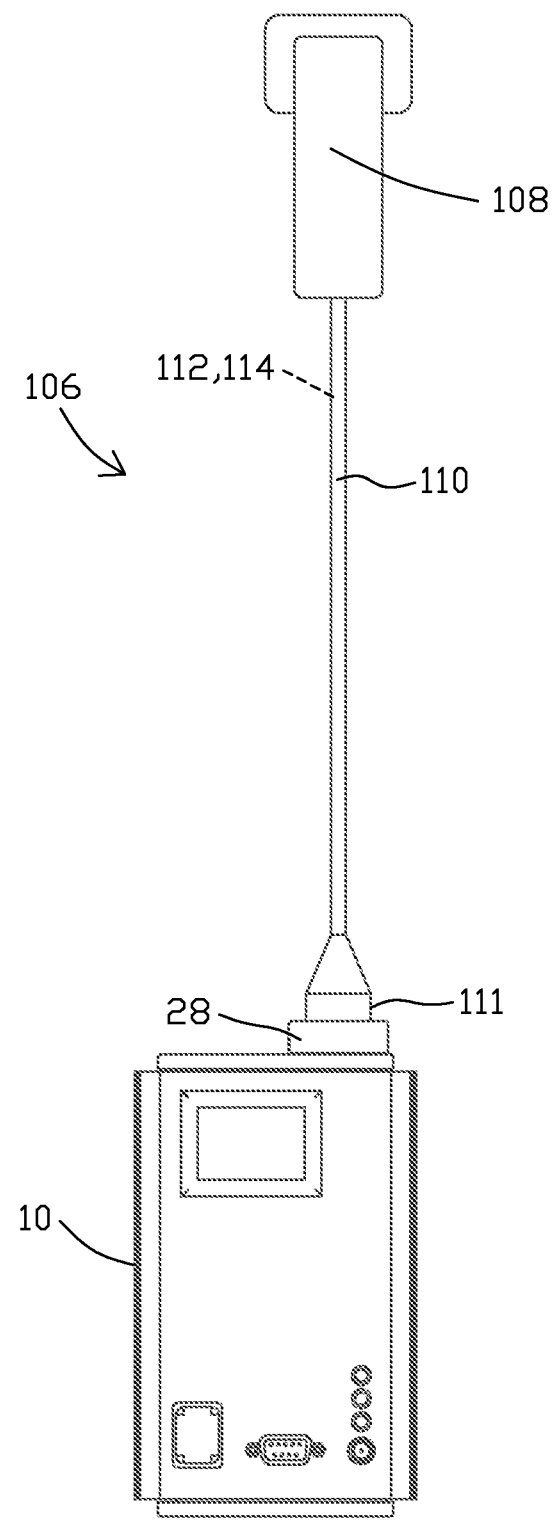
FIG. 8 is a perspective view showing a system for measuring $StO_2$ in accordance with an illustrative embodiment.
Figure 9:
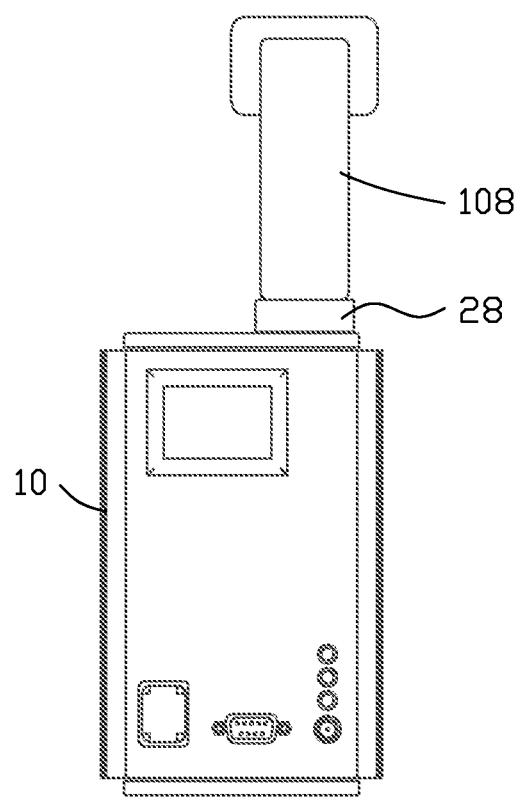
FIG. 9 is a perspective view showing a system for measuring $StO_2$ in accordance with another illustrative embodiment.

FIG. 8 is a perspective view of an $StO_2$ monitor 10 connected to a patient sensor interface 108 as part of a system 106 for measuring $StO_2$ in accordance with an illustrative embodiment. As shown in FIG. 8, the patient sensor interface 108 is connected to the monitor 10 via an optical cable 110, and includes an optical connector 111 that connects to the sensor connector 28 on the monitor 10. The optical cable 110 houses a number of optical fibers or fiber bundles 112,114 (hidden) configured for transmitting and receiving NIR light. In an alternative embodiment shown in FIG. 9, the optical cable 110 can be omitted and the patient sensor interface 108 connected directly to the sensor connector 28 on the monitor 10, if desired.

During operation, light transmitted from the optical sourcing and receiving unit 50 is directed to the sensor connector 28, through a transmit fiber or fiber bundle 112 in the optical cable 110, and into the tissue via a transmit port on the patient interface 108. Radiation reflected from tissue at the measurement site is transmitted back to the optical converter 52 via a second, receive port on the patient interface 108, and is then delivered via a fiber or fiber bundle 114 within the optical cable 110 to a receive fiber 116 within the optical sourcing and receiving unit 50, as further shown in FIGS. 4-5. A similar scheme can be employed for connecting the patient sensor interface 108 to the other types of monitors, including monitor 30 shown and described with respect to FIG. 2.

Patient interfaces or sensors of differing configurations may be releasably connected to the portable $StO_2$ monitor 10 via the sensor connector 28. In some embodiments, an optical connector such as that disclosed, for example, in U.S. Pat. No. 7,165,893 to Schmitz may be used. For a given sensor configuration, the optical connector may be incorporated directly into the patient sensor interface 108, or may be extended from the sensor interface body via an optical cable 110.

Figure 10:
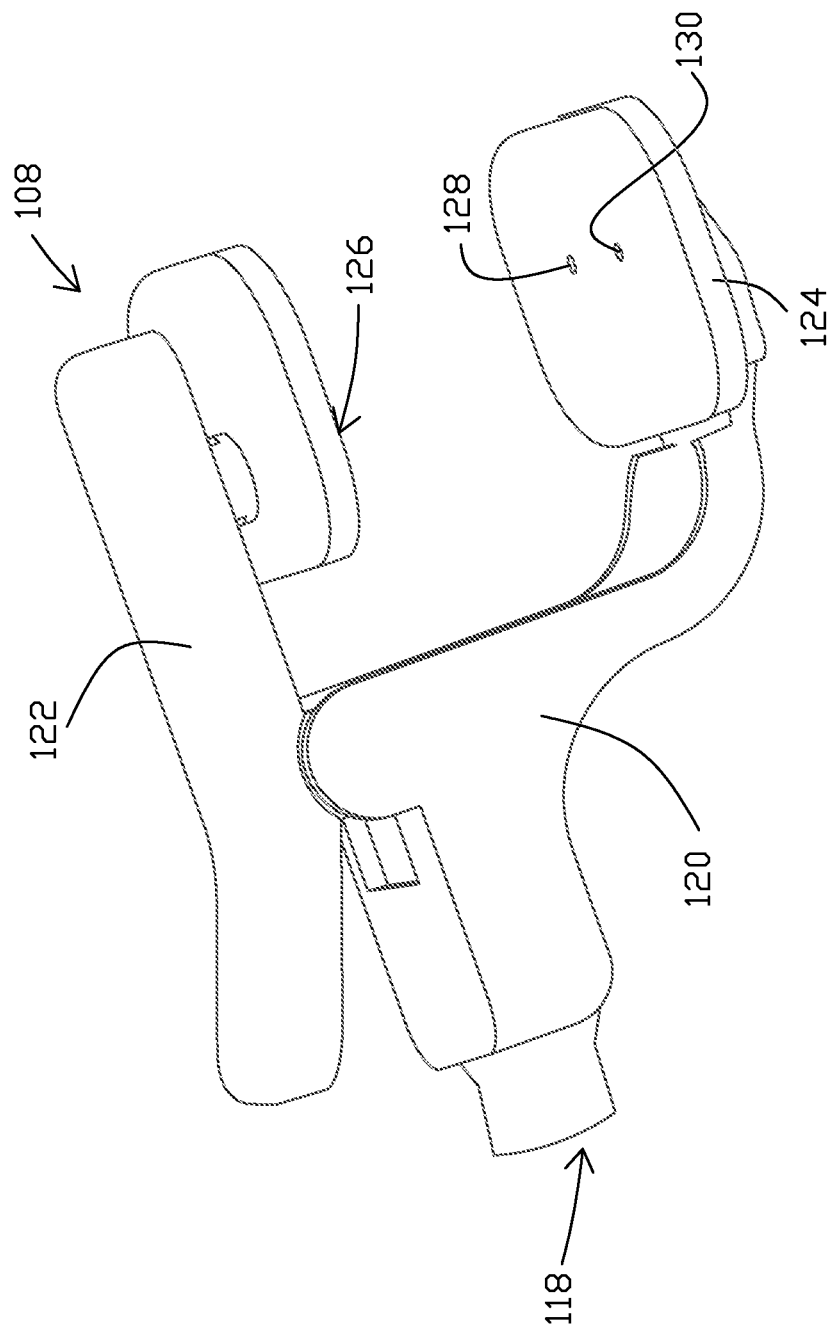
FIG. 10 is a perspective view showing a sensor patient interface in accordance with an illustrative embodiment.

FIG. 10 is a perspective view showing a sensor patient interface 108 in accordance with an illustrative embodiment. In the embodiment shown, the patient interface 108 comprises a spring clip having an optical cable connector 118, a signal interface arm member 120, a pivoting clamp force arm member 122, a signal interface pad 124, and a gimballing pressure pad 126. The signal interface pad 124 may be pivotally connected to or integral with arm member 122, and includes measurement and reflected radiation ports 128,130 optically connected to the optical signal converter 52 via the fibers or fiber bundles 112,114 described above.

Figure 11:
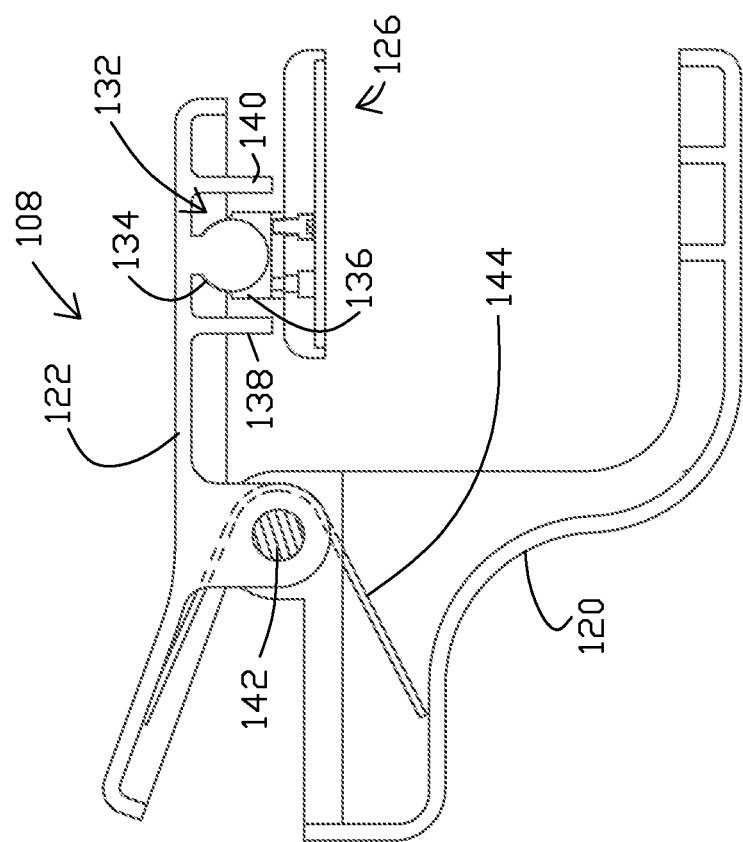
FIG. 11 is a partial cross-sectional view of the sensor patient interface of FIG. 10.
Figure 12:
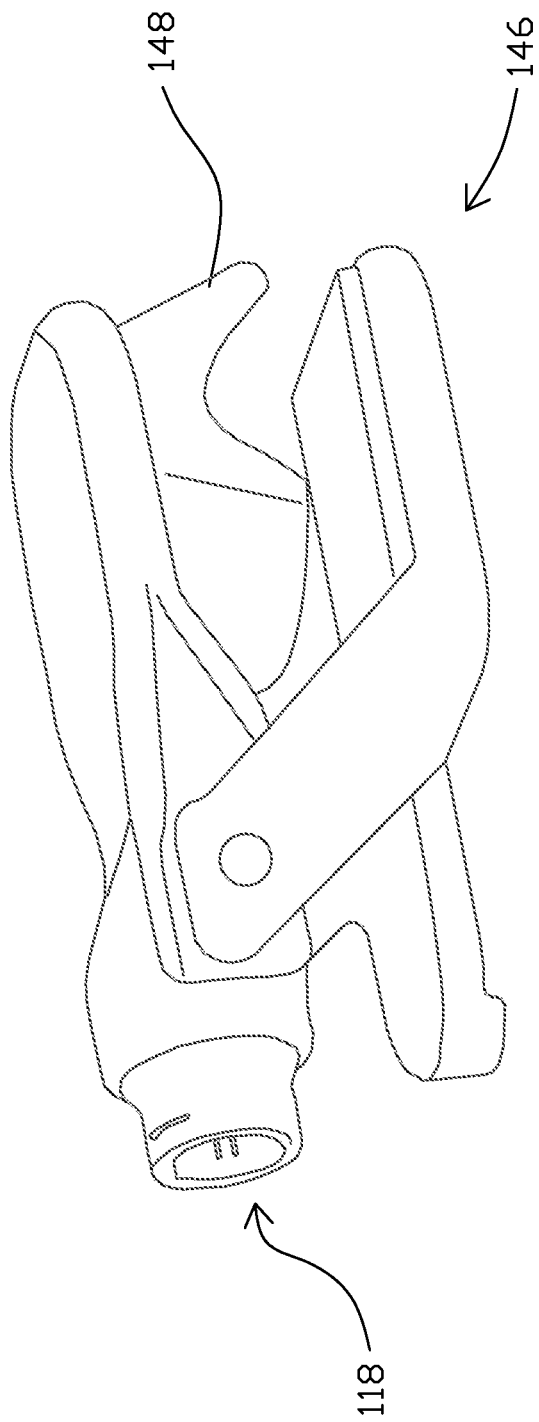
FIG. 12 is a perspective view showing a sensor patient interface in accordance with another illustrative embodiment including a pressure dispersion pad.

As further shown in FIG. 11, the gimballing pressure pad 126 is connected to the clamp force member 122 via a ball-and-socket joint 132 to provide for pitch, roll and yaw rotational movement. In the illustrated embodiment, a ball 134 is molded into or otherwise integrated with the clamp force member 122, and the gimballing pressure pad 126 is attached to the ball 134 via a socket assembly 136. Stand-offs 138,140 on the clamp force member 122 are configured to limit excessive pitch, roll and yaw of pressure pad 126.

A pivot pin 142 and spring 144 coupled to the signal interface arm member 120 and clamp force member 122 biases the two members 120,122 together to exert a clamping force on the patient's extremity (e.g., hand). The clamping force provided by the spring 144 is dispersed via the surface area of the signal interface pad 124 and the gimballing pressure pad 126 so that blood flow to the patient measurement site is not adversely affected. The sensor clip 108 can be configured to provide a constant or nearly constant clamping pressure regardless of patient hand size through the use of a low spring rate spring or the like. In some embodiments, the sensor interface pad 124 and the gimballing pressure pad 126 can be fitted with gel or foam pieces to enhance patient comfort. In another alternative embodiment shown in FIG. 12, an illustrative spring clip patient interface 146 includes a comfort enhancing, cup-shaped pressure dispersion pad 148 in place of a gimballing pressure pad. The pressure dispersion pad 148 may be made from gel, foam or other suitable material.

Figure 13:
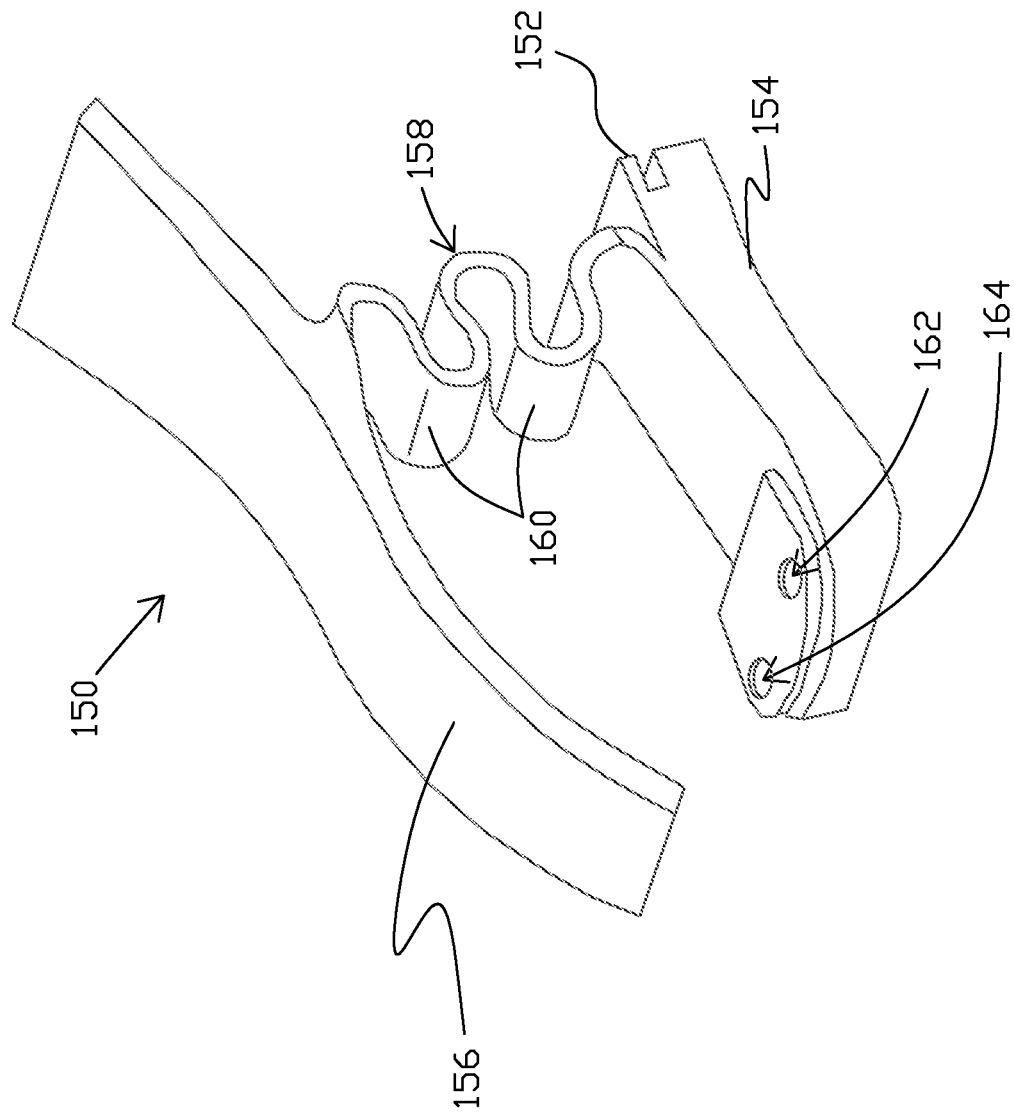
FIG. 13 is a perspective view showing a sensor patient interface in accordance with another illustrative embodiment including a spring.
Figure 14:
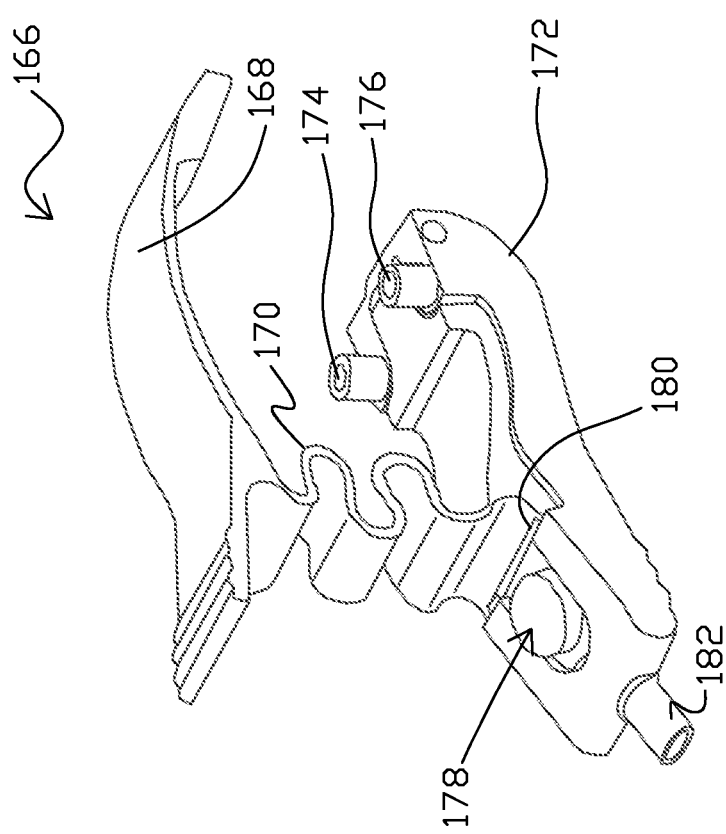
FIG. 14 is a perspective view showing a sensor patient interface in accordance with another illustrative embodiment including a spring.

FIG. 13 is a perspective view showing a sensor patient interface 150 in accordance with another illustrative embodiment including a low spring rate spring. As shown in FIG. 13, the patient interface 150 comprises a spring clip including an optical cable connector 152, a number of arm members 154, 156, and a low spring rate spring 158 or the like configured to provide a nearly constant clamping pressure regardless of patient hand size. The spring 158 can include a number of zigzags or other bending spring elements 160 configured to increase the effective chord length of the spring 158. Increasing the effective length of the spring 158 reduces the spring constant, which in turn decreases the change in force over the dynamic range of the clip motion. The position and the size of the spring 158 also affects the center of rotation of the clip 150. Various design parameters of the spring 158, including its position, size and composition, can be selected so as to impart a desired spring force characteristic to the spring 158.

A number of radiation ports 162,164 in one or both of the arm members 154,156 are optically connected to the optical signal converter 52 via optical fibers or fiber bundles 112,114, as discussed previously. In use, light signals are transmitted into the patient tissue through one of the radiation ports (e.g., port 162) and is then received back from the tissue through another radiation port (e.g., port 164) and transmitted via the optical cable 110 back to the optical sourcing and receiving unit 50. In another embodiment, a single, larger radiation port can be employed for both transmitting and receiving light at the patient measurement site. In some embodiments, the arm member 154 containing the radiation ports 162,164 comprises a plastic molded piece that has a clearance or space for the optical cable 110 to pass through the arm 154 and adjacent to the entrance/exit of the ports 162,164.

In the embodiment of FIG. 13, the arm members 154,156 and spring 158 comprise a single piece or structure. The arm members 154,156 and spring 158 can comprise, for example, molded or machined one piece polycarbonate or polyoxymethylene (e.g., Delrin™). Alternatively, and in other embodiments, the spring clip 152 can comprise multiple parts or pieces that are assembled together. In one alternative embodiment shown in FIG. 14, for example, a spring clip 166 comprising multiple parts or pieces includes a first spring arm member 168 with a spring 170 as a first part, and a second spring arm member 172 with a number of optical ports 174, 176 as a second part. The spring 170 can include an inner spring structure fabricated from polycarbonate or polyoxymethylene, and an outer skin or overmold fabricated from silicone. A release button 178 engages a tab 180, which is used to secure the two arm members 168,172 together. An optical cable port 182 on the second spring arm member 172 is configured to receive the optical cable 110. In use, the use of multiple parts or pieces for the spring clip 166 provides the benefit of reducing the number of parts required for disposal with each new use of the monitor 10,30.

Figure 15:
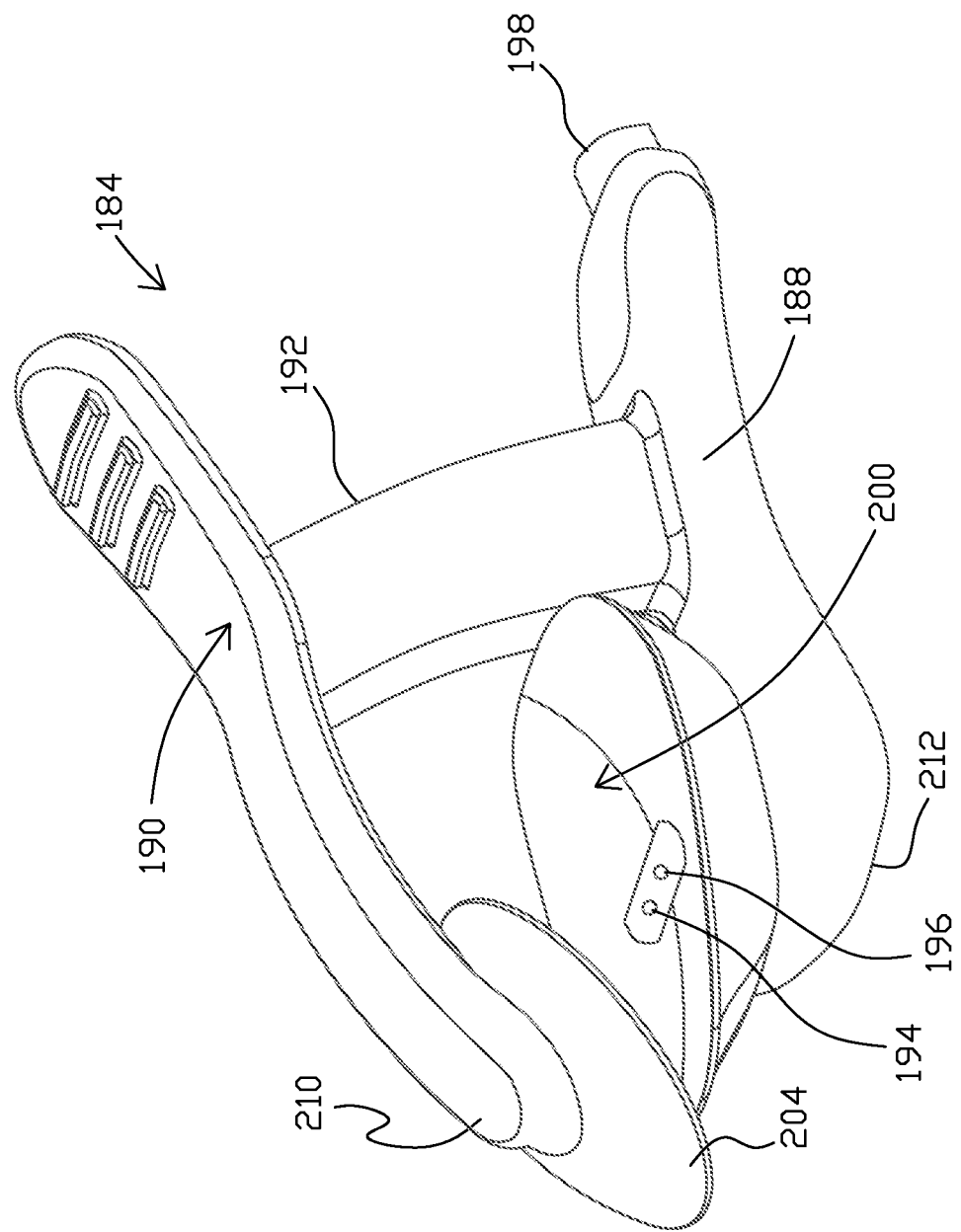
FIG. 15 is a perspective view showing a sensor patient interface in accordance with another illustrative embodiment.

FIG. 15 is a perspective view showing a sensor patient interface 184 in accordance with another illustrative embodiment including a light shield. As shown in FIG. 15, the patient interface 184 comprises a spring clip including a number of arm members 188,190 and a low spring rate spring 192 or the like configured to provide a constant or near constant clamping pressure regardless of patient hand size. A number of radiation ports 194,196 on one or both of the arm members 188,190 are optically connected to the optical signal converter 52 via optical fibers or fiber bundles 112,114, as discussed previously. An optical cable port 198 on the arm member 188 is configured to receive the optical cable 110 for optically connecting the patient interface 184 to a monitor 10,30.

In the embodiment of FIG. 15, the patient interface 184 further includes a light shield 200 and a pad 204. The light shield 200 includes a number of shield ports in optical communication with the radiation ports 194,196 to allow light to pass through the light shield 200. In use, the spring 192 is configured to bias the ends 210,212 together, causing the light shield 200 and pad 204 to clamp onto the patient's hand or other body part. When attached, the light shield 200 is configured to allow only that light transmitted through the optical cable 110 and into the ports 194,196 from reaching the body tissue at the measurement site.

Figure 16:
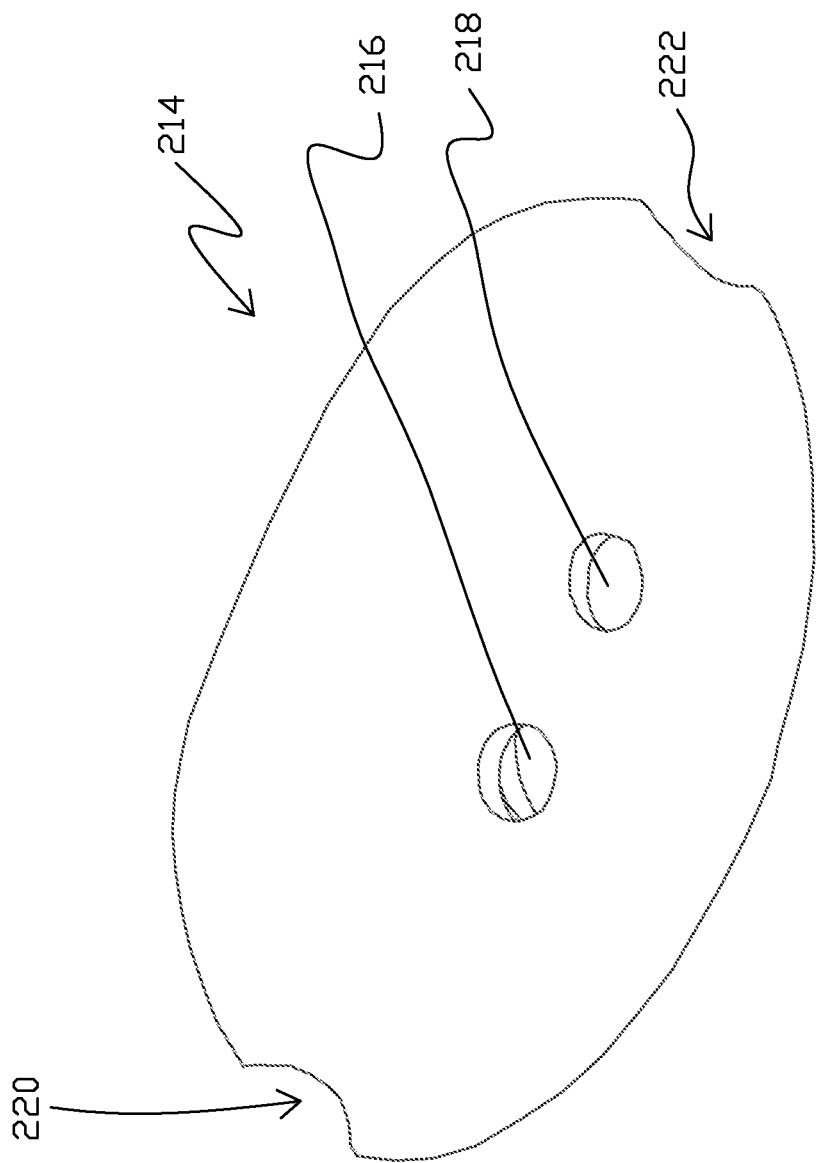
FIG. 16 is a perspective view showing a light shield for use with a sensor patient interface in accordance with an illustrative embodiment.
Figure 17:
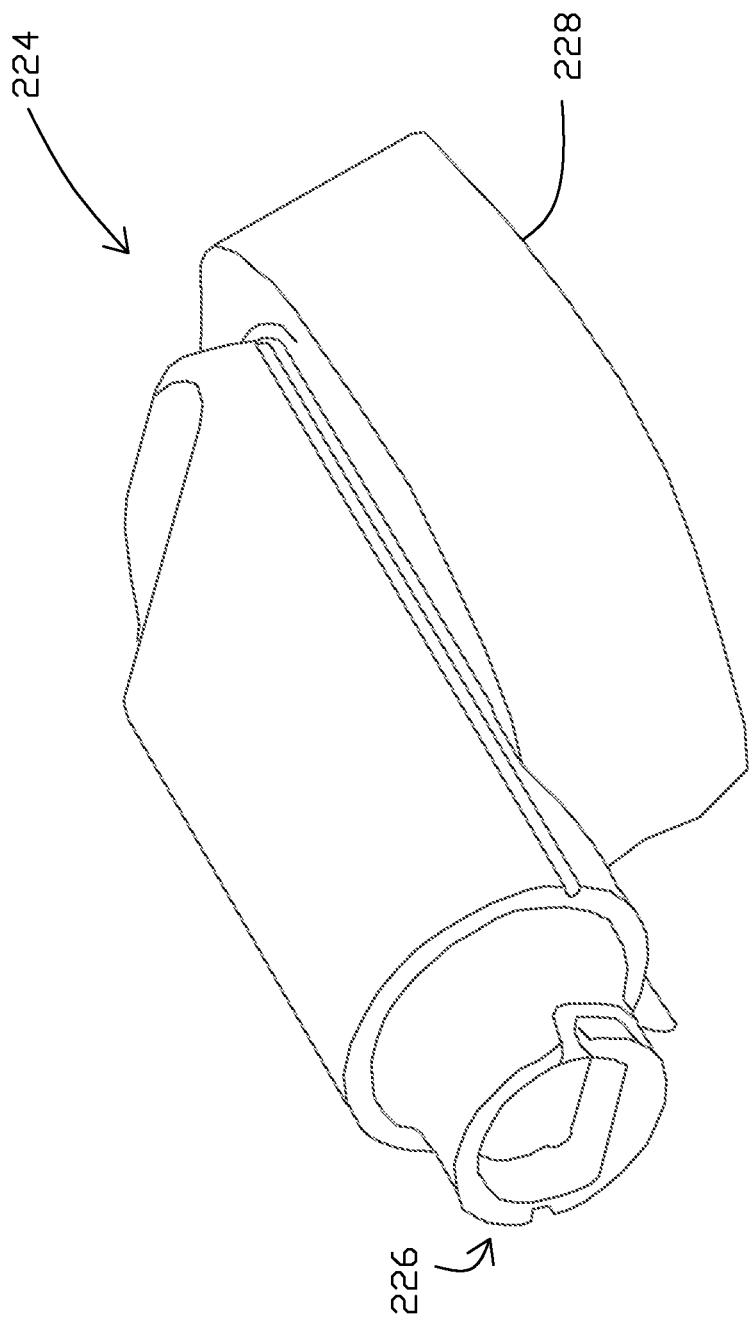
FIG. 17 is a perspective view showing a sensor patient interface in accordance with an illustrative embodiment adapted to be held in place during use.
Figure 18:
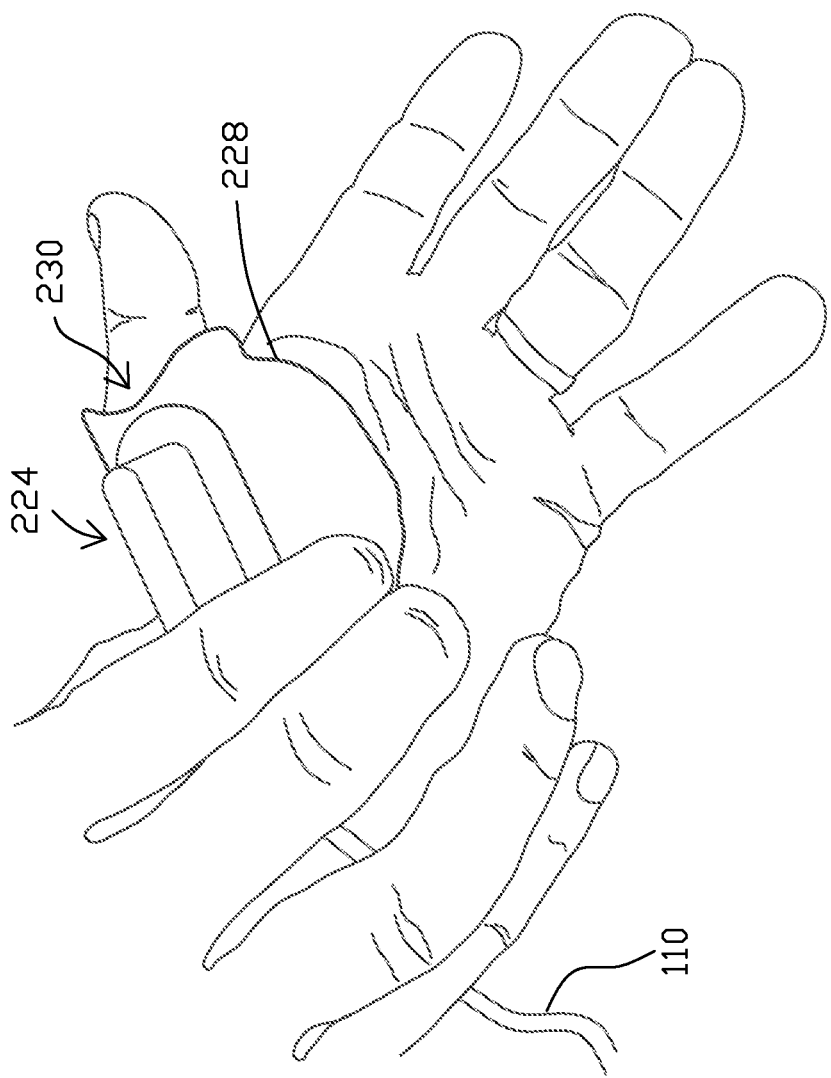
FIG. 18 is a view showing the sensor patient interface of FIG. 17 coupled to a patient's hand.
Figure 19:
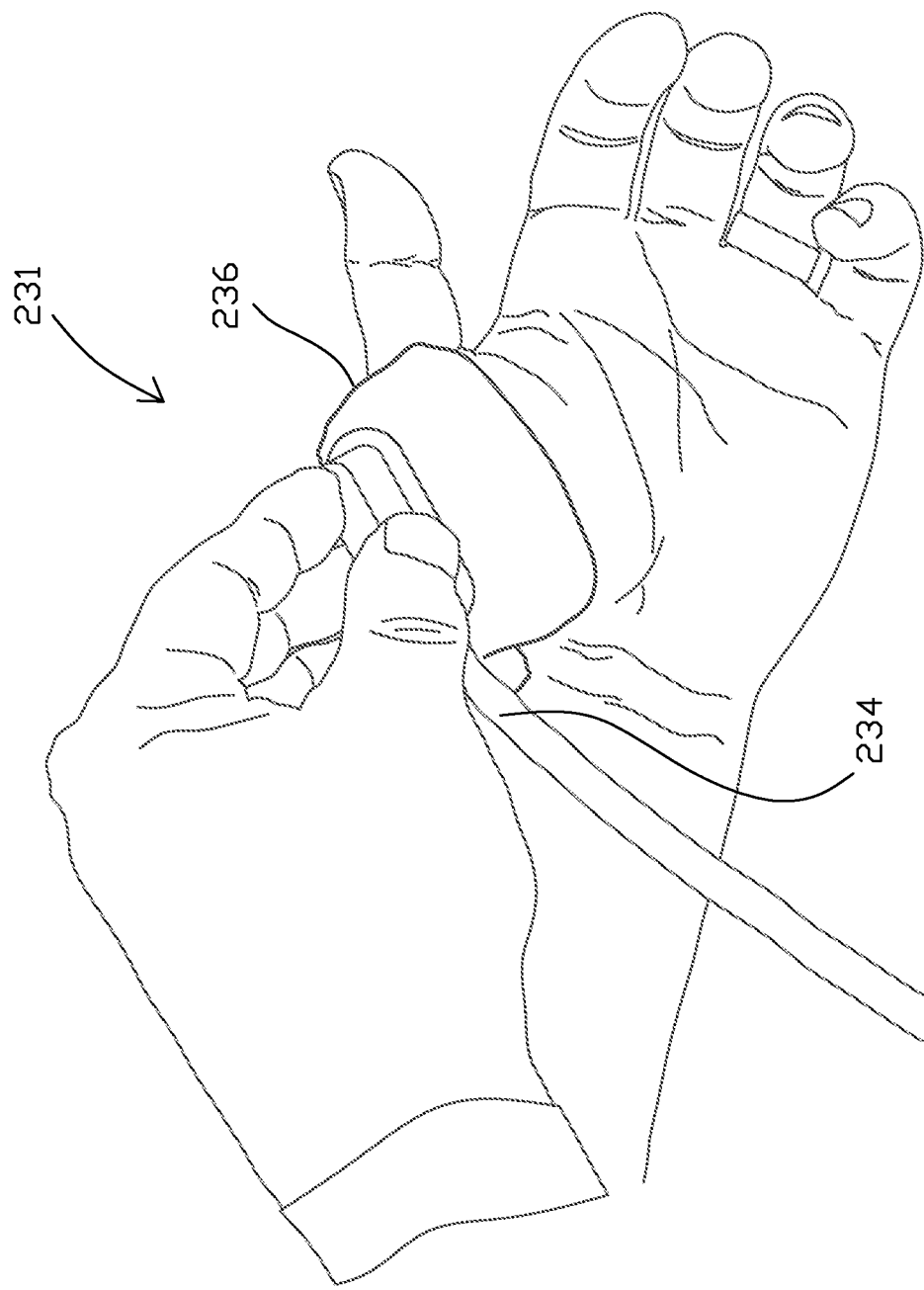
FIG. 19 is a view showing another illustrative sensor patient interface coupled to a patient's hand.

FIG. 16 is a perspective view showing a light shield 214 for use with a sensor patient interface in accordance with an illustrative embodiment. As shown in FIG. 16, the light shield 214 includes a number of shield ports 216,218 and locating features 220,222. The shield ports 216,218 are in optical communication with the radiation ports on the patient interface (e.g., ports 194,196) to allow light from the optical cable 110 to be transmitted into and received from the tissue. The locating features 220,222 can be used, for example, as an aid to align the shield ports 216,218 along a desired body feature such as the thenar eminence of the hand. The light shield 214 can be made from a flexible material such as silicone, and is generally opaque to visual and NIR light to prevent undesired light from interfering with the light entering and exiting the body tissue through the ports 216,218.

In some embodiments, the sensor patient interface is configured to be manually held in place during StO$_2$ sensing. In one such embodiment shown in FIG. 17, for example, a sensor patient interface 224 includes an optical connector 226 and a cup-shaped pressure dispersion pad 228. The pressure dispersion pad 228 is shaped so as to not impede blood flow to the measurement site. As can be further seen in FIG. 18, a locating feature 230 is configured to help align the patient interface 224 with the thenar eminence, as shown. Another illustrative sensor patient interface 230 including an optical connector 234 and a cup-shaped, foam pressure dispersion pad 236 with a concave portion carved out on the patient facing surface is further shown in FIG. 19.

Figure 20:
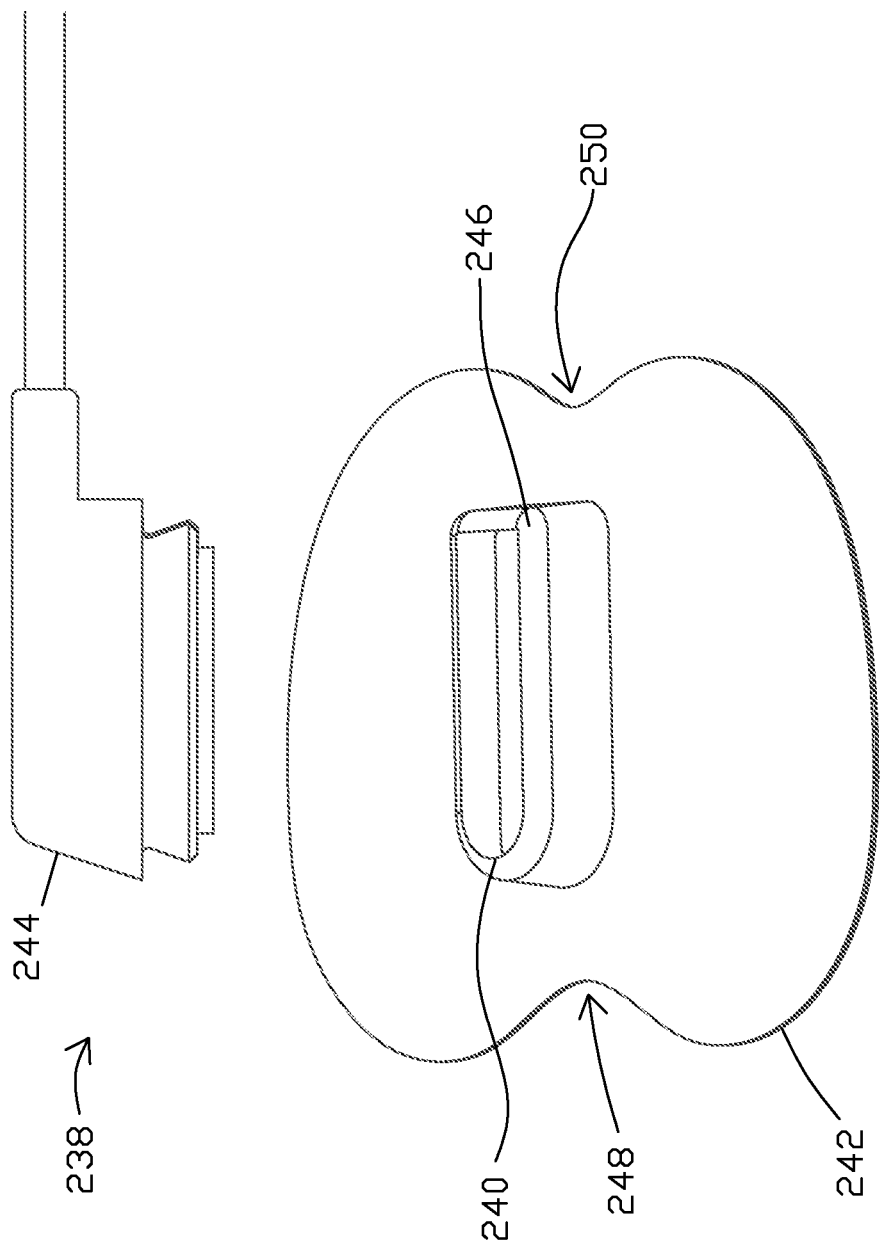
FIG. 20 is a perspective view showing a sensor patient interface in accordance with another illustrative embodiment adapted to be held in place during use.
Figure 21:
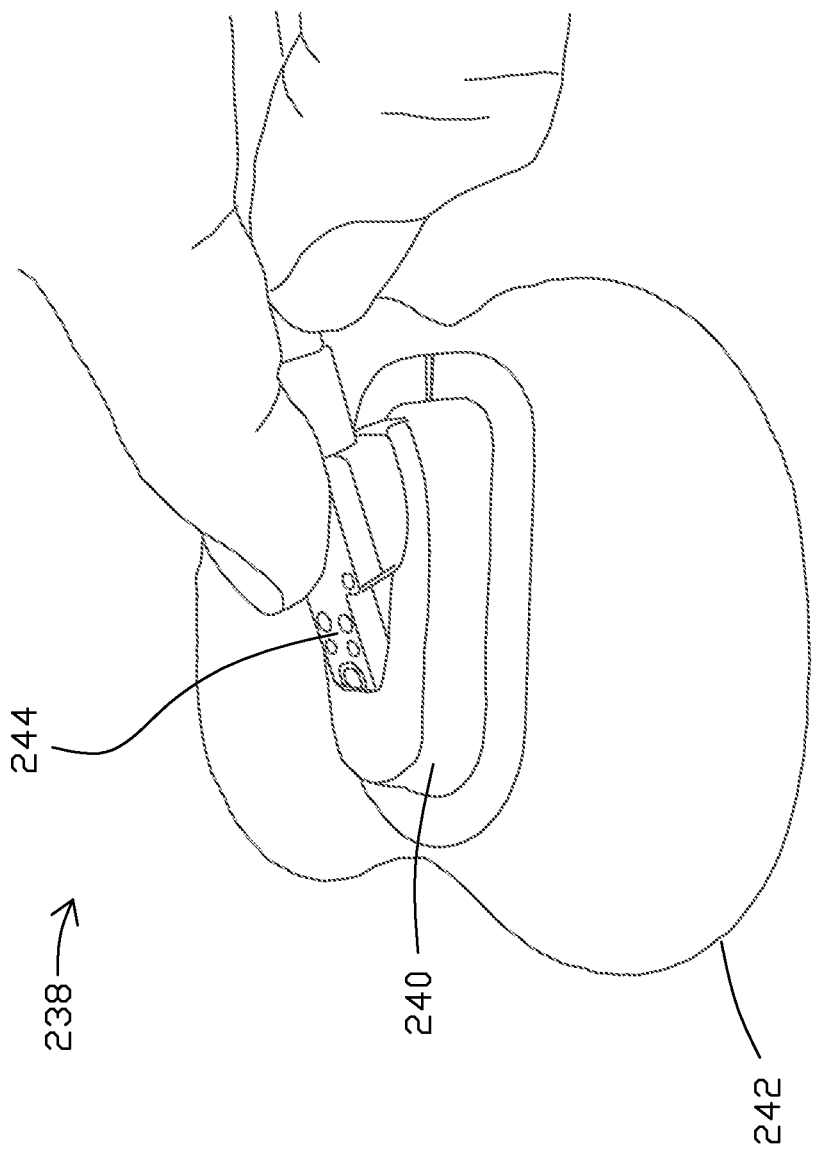
FIG. 21 is another perspective view showing the insertion of the sensor unit of FIG. 20 into the pressure dispersion pad.
Figure 22:
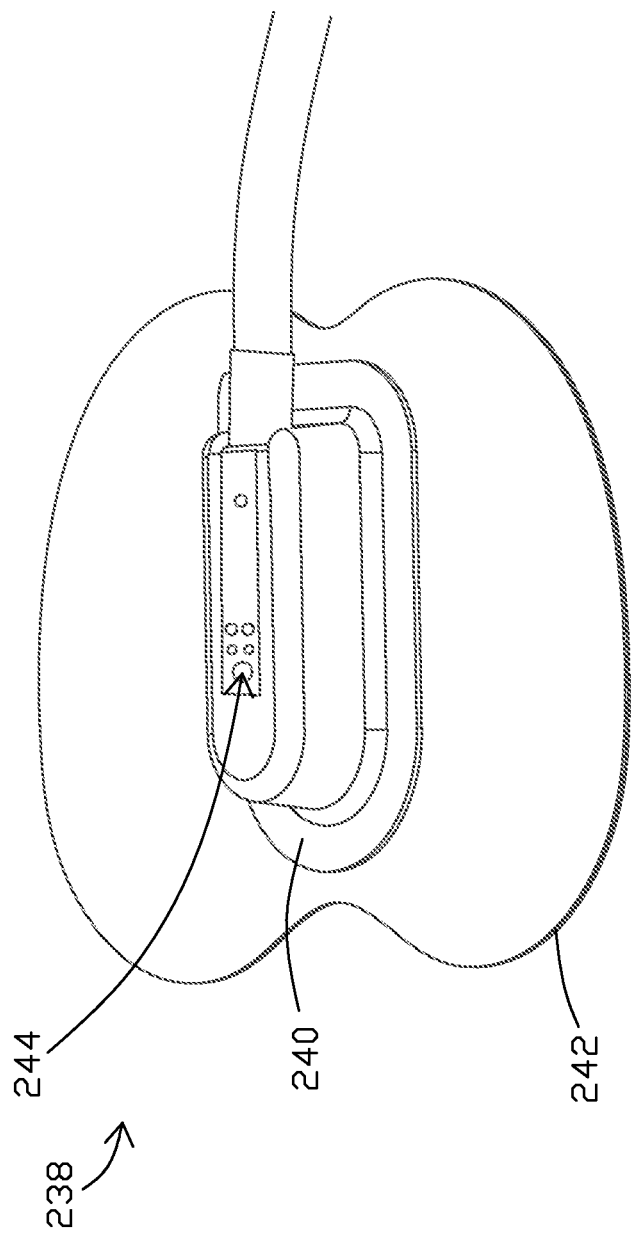
FIG. 22 is another perspective view showing the sensor unit of FIG. 20 fully inserted within the pressure dispersion pad.
Figure 23:
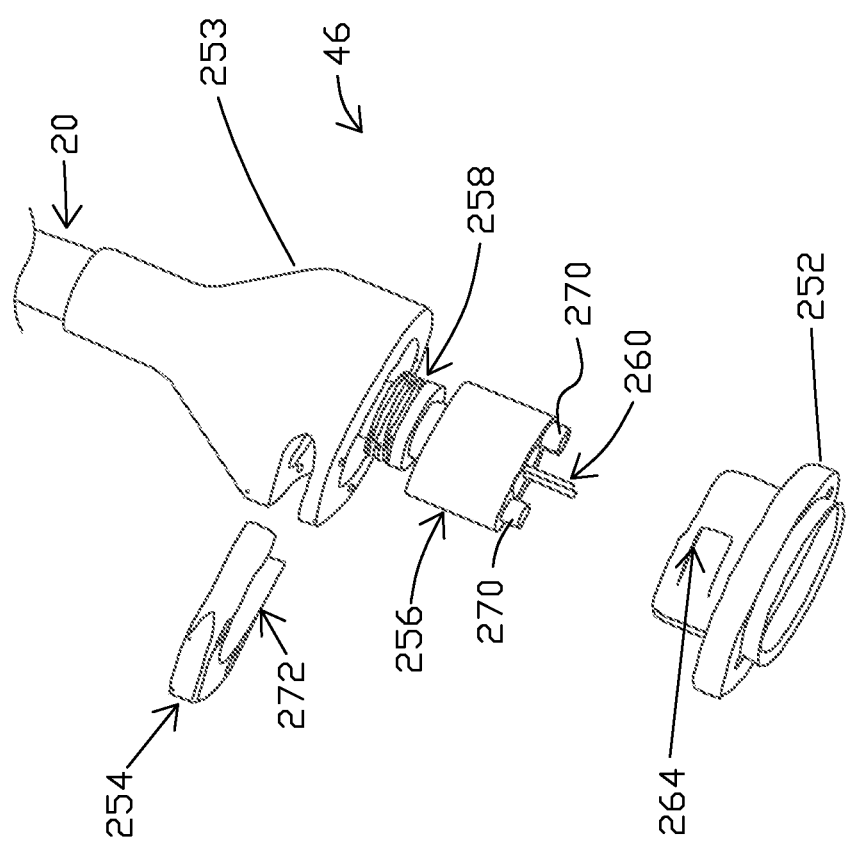
FIG. 23 is an assembly view showing an electro-optical sensor connector in accordance with an illustrative embodiment.
Figure 26:
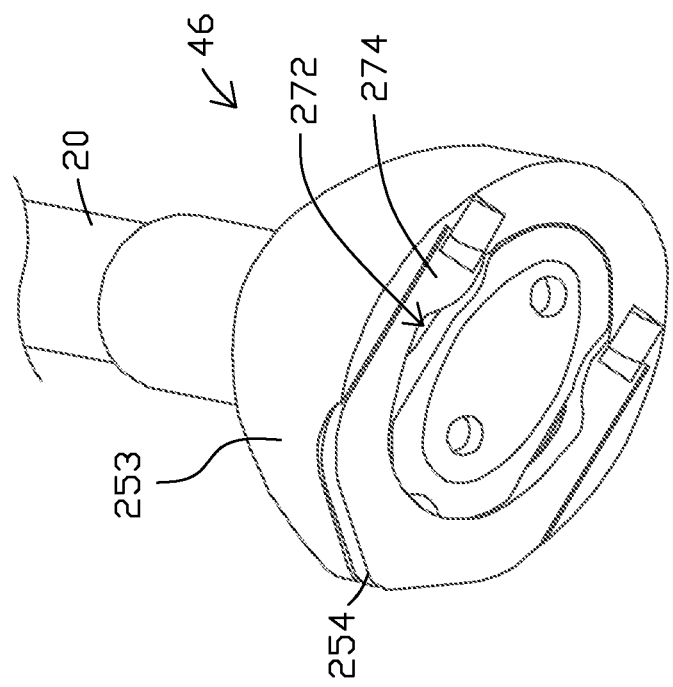
FIG. 26 is a cross-sectional view showing the electro-optical sensor connector when the push button is in the engaged position.
Figure 27:
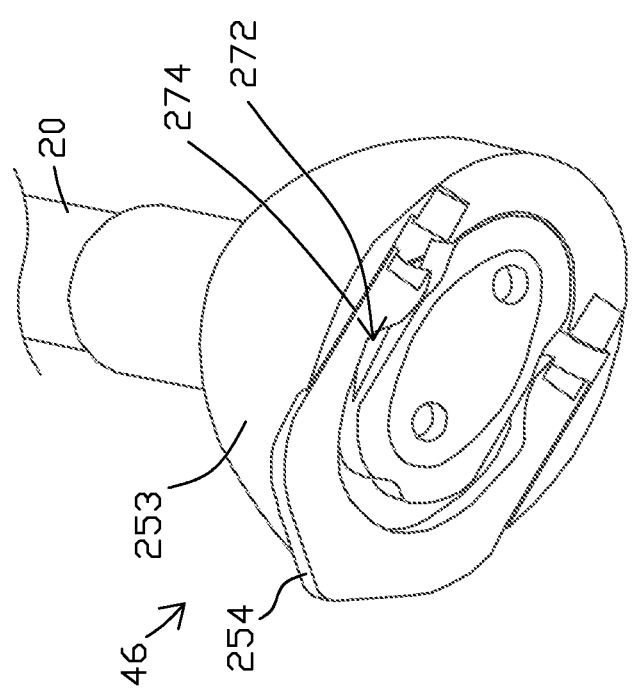
FIG. 27 is a cross-sectional view showing the electro-optical sensor connector when the push button is in a disengaged position.

In one embodiment configured for hand-held use in FIG. 20, a patient interface 238 includes a pressure dispersion pad 240 incorporated into an adhesive backed member 242 such as the Model 650 InSpectra™ patient interface described, for example, with respect to U.S. Pat. No. 7,460,897 to Flessland et al., which is incorporated herein by reference in its entirety for all purposes. As shown in FIG. 20, the patient interface 238 includes a sensor tip 244 that can be releasably coupled to a base 246 of the pad 240. The foam cap portion 242 of the pad 240 includes a number of locating features 248,250 configured to help align the patient interface 238 with the thenar eminence. During assembly, the sensor tip 240 can be inserted into the base 246 of the pad 240 by inserting one end of the sensor tip 240 into the base 246, as shown in FIG. 21, and then pushing the other end of the sensor tip 240 downwardly until the remainder of the sensor tip 240 is fully engaged in the base 246, as further shown in FIG. 22. After use, the sensor tip 240 can be removed from the base 246, allowing the pad 240 to be discarded. The sensor tip 240 can then be reused with another dispersion pad 240, if desired.

Other patient interface designs may also be used with the StO$_2$ monitor 10,30. For example, a glove-interface or bandage-wrap interface can be utilized in some embodiments. Examples of other patient interfaces are disclosed in U.S. Pat. No. 7,460,897 to Flessland et al. and U.S. Pat. No. 6,839,583 to Lewandowski et al., each of which are incorporated herein by reference in their entirety for all purposes. The Flessland et al. patent discloses a patient interface optically connected to one half of the optical connector disclosed in U.S. Pat. No. 7,165,893 to Schmitz via an optical fiber bundle. The patient interface disclosed in the Flessland et al. patent includes an adhesive layer for temporary attachment to the measurement site. Like the spring clip design, the adhesive layer allows for leaving the patient interface sensor attached to the patient while being disconnected from the StO$_2$ monitor. The Lewandowski et al. patent, in turn, discloses a patient interface having a disposable elastomeric base member designed to releasably engage an optical probe. The elastomeric base of Lewandowski et al. also includes adhesive on the tissue-engaging surface for securing and leaving the base member attached to the measurement site of the patient while being disconnected from the StO$_2$ monitor. In some embodiments, the patient interface may be modified or combined with that of the Flessland et al. and Lewandowski et al. patient interface designs.

FIGS. 23-27 are several views showing an electro-optical sensor connector 46 in accordance with an illustrative embodiment. As shown, the connector 46 is configured to engage a receiver 252 of the monitor 10,30 to releasably connect the optical cable 45,110 with the optical sourcing and receiving unit 50 discussed herein. The connector 46 includes a connector housing 253, a push button 254, a ferrule 256, a spring 258, and a number of electrical connectors 260. The receiver 252 includes a tab 262 having a wedge 264 that engages a notch 266. A seal 268 within the interior of the receiver 252 is configured to provide a seal between the receiver 252 and the connector 46 to prevent moisture and debris from entering the connector housing 253 when the connector 46 is not engaged with the receiver 252, as discussed further herein. A number of optical locating features 270 allow for light from fiber optics cable 20 to pass through the connector 46 and receiver 252 to the optical sourcing and receiving unit 50.

When connecting the connector 46 to the receiver 252, the wedge 264 is configured to move along a wedge 272 on an interior portion of the push button 254 until the tab 264 is engaged in the notch 266, as shown, for example, in an engaged position in FIG. 24. To disengage the connector 46 from the receiver 252, and as further shown, for example in FIG. 25, the push button 254 is depressed so that a disengagement wedge 274 (see FIGS. 26-27) causes outward movement of the portions of the push button 254 that engage the notch 266. The ferrule 256 has at least some degree of freedom of movement within the connector housing 253 to move, but is generally biased towards the receiver 252 via the spring 258. An electrical chip 275 is configured to track the amount of usage of the optical cable 40,110, and in some embodiments can be stored with the cable 44,110 and used to correct manufacturing variations in optical cable attenuation.

Figure 28:
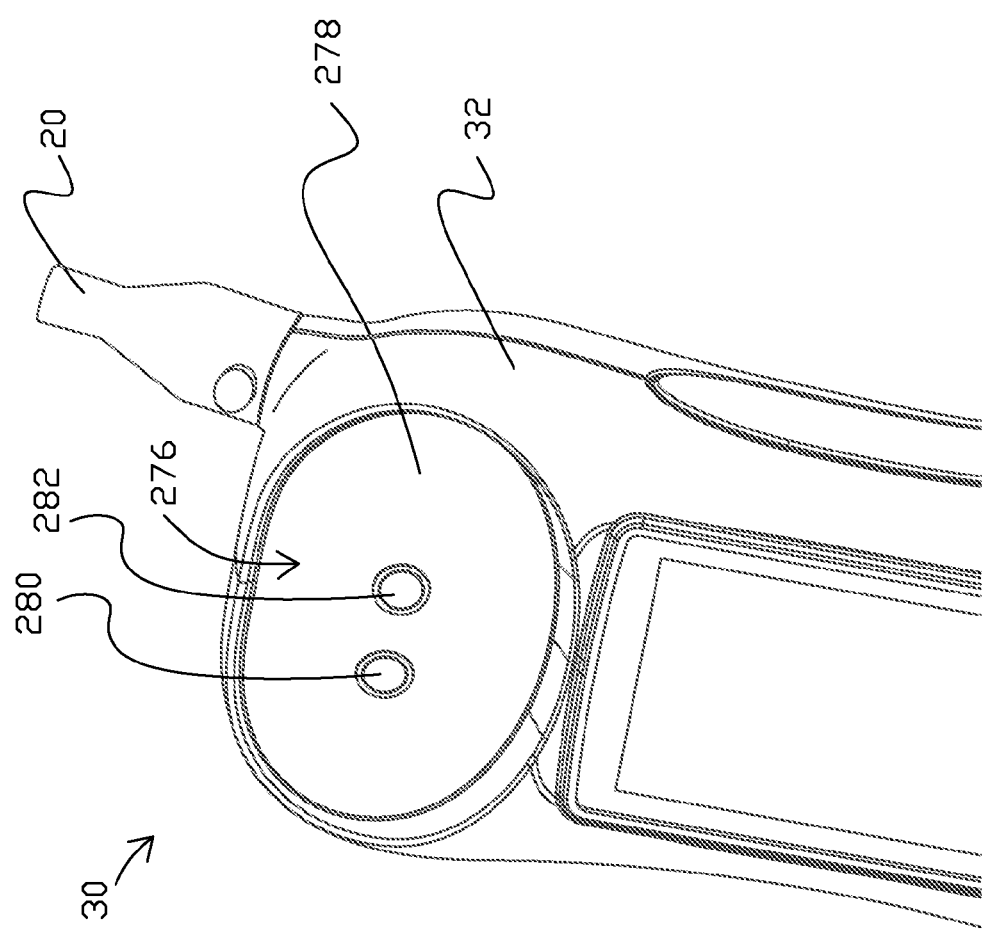
FIG. 28 is a perspective view showing a portable, hand-held $StO_2$ monitor including a testing interface in accordance with an illustrative embodiment.
Figure 29:
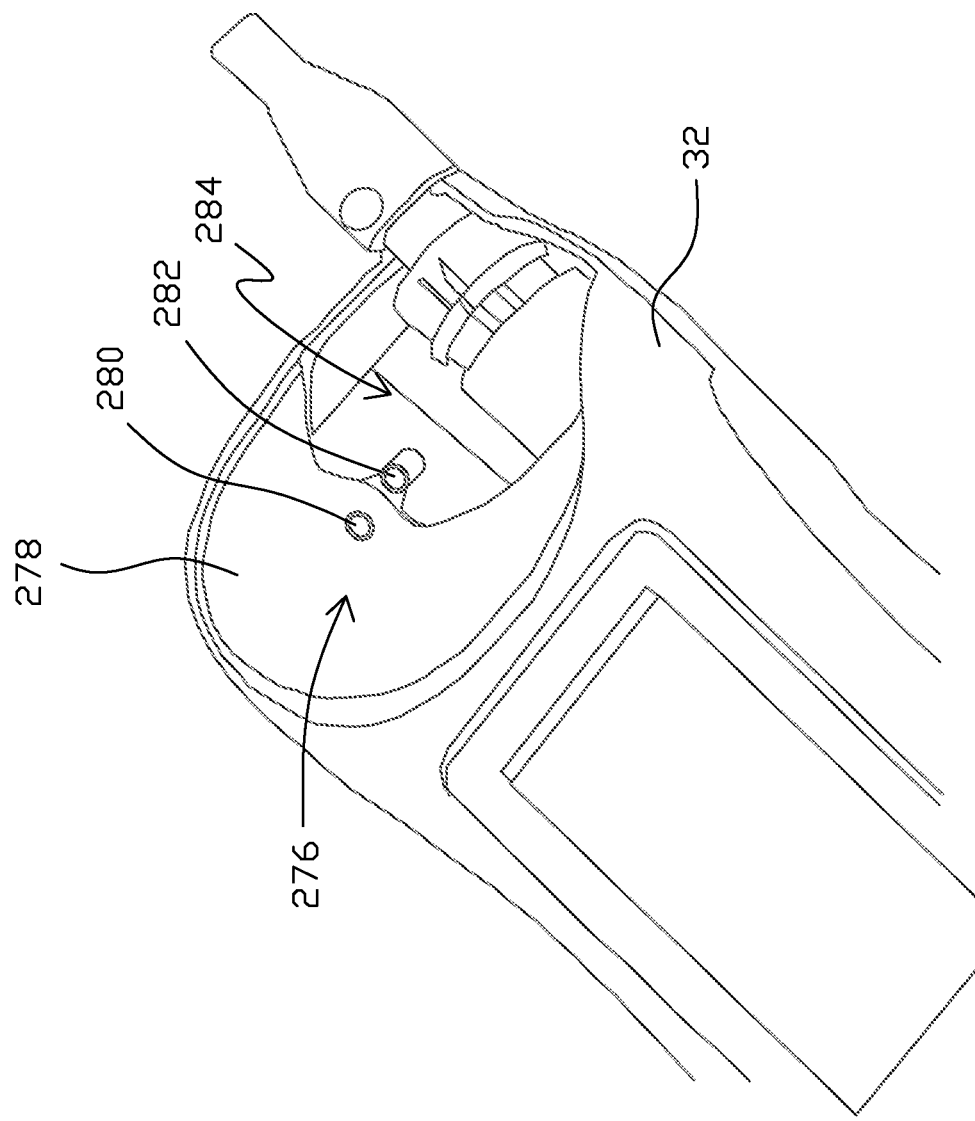
FIG. 29 is a broken perspective view showing several example components of the portable, hand-held monitor of FIG. 28.

FIGS. 28-29 are several views showing a portable, hand-held StO$_2$ monitor 30 including a testing interface 276 in accordance with an illustrative embodiment. As shown, the monitor housing 32 includes a an external clip area 278 for holding a patient interface when not in use on a patient. The clip area 278 of the housing 32 includes a number of optical ports 280,282 in optical communication with the radiation ports of the patient interface. By way of example and not limitation, the ports 280,282 can be configured to communicate with the radiation ports 194,196 described with respect to patient interface 184 of FIG. 15. During testing, and as further shown in FIG. 29, the ports provide an optical path to a test module 284 located within the monitor 30, which can be used to test the operation of the monitor 30 and/or the patient interface.

Figure 30:
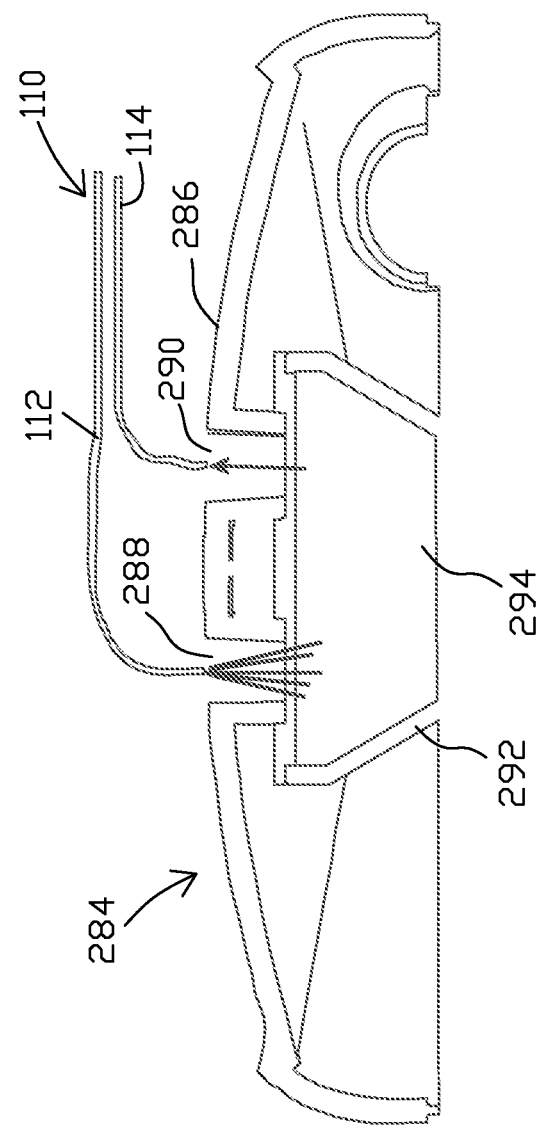
FIG. 30 is a cross-sectional view of the portable, hand-held monitor of FIG. 28 showing the testing interface in greater detail.

FIG. 30 is a cross-sectional view of the portable, hand-held monitor 30 of FIG. 28, showing the test module 284 in greater detail. As can be further seen in FIG. 30, the test module 284 includes a shell 286 with a number of windows 288,290, an enclosure 292, and a bulk scattering member 294 such as foam, epoxy/glass beads, epoxyTiO$_2$, or the like. The windows 288,290 may be filled with an optical conductor such as acrylic, and are configured to provide an optical path through the shell 286. An example foam material that can be used for the foam 294 is Plastazote® LD45 produced by Zotefoams Inc. of Walton, Ky. The light scattering properties provided by the foam 294 is generally spectrally flat (i.e., reflects all light to the same degree) to provide a reference spectrum.

During a self test mode of operation, light from the optical cable 110 enters through one of the windows 288, passes through the foam 294, and is collected again by the optical cable 110 through another window 290. Calibration procedures can be performed to enhance the accuracy of the measurements subsequently made by the instrument. The system check provides an attenuated optical signal from the spectrometer light source to the spectrometer detection system within the usable dynamic range of the system. The associated absorbance values for each wavelength are adjusted with electronic offsets to achieve, in some embodiments, the nominal 2nd derivatives corresponding to a StO$_2$ of 50 and THI of 10 when measured on a device with an accurate reference. The test module 284 serves as a device to compare the compensated relative intensity of the light sources to the relative intensities when the monitor 30 is referenced at the factory. Light in the transmission fiber should be sampled uniformly (both spatially and angularly), and should be attenuated to a level that does not saturate the detectors. Preferably, attenuation by the foam 294 does not change with time, temperature or humidity. If attenuation does change, however, the attenuation should change equally for all light sources (i.e., by the same percentage change). Methods and devices for calibrating spectrophotometric-type instruments are generally known and disclosed, for example, in U.S. Pat. No. 5,879,294 to Anderson et al., which is incorporated herein by reference in its entirety for all purposes.

FIGS. 31A-31J are several screen-shots showing an illustrative graphical user interface (GUI) for a portable, hand-held StO$_2$ monitor in accordance with an illustrative embodiment. FIGS. 31A-31J may represent, for example, several illustrative display screens that can be displayed on the digital displays 14,36 for the exemplary monitors 10,30 described above with respect to FIGS. 1 and 2, respectively. In addition, or in lieu, FIGS. 31A-31J may represent several display screens that can be displayed on a monitor of another device (e.g., a computer terminal) connected to the monitor 10,30.

Figure 31B:
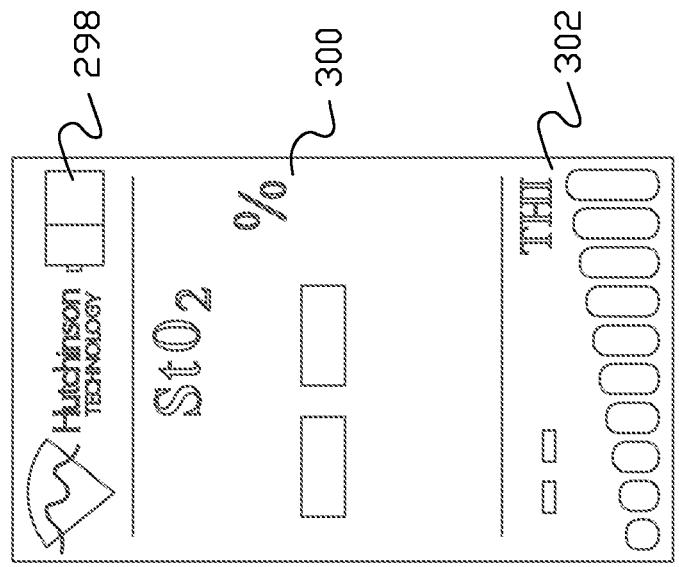
Figure 31A:
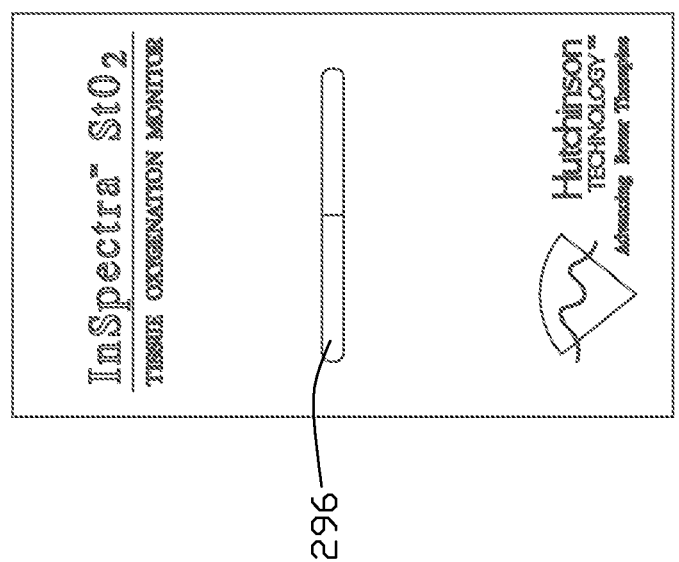
Figure 31D:
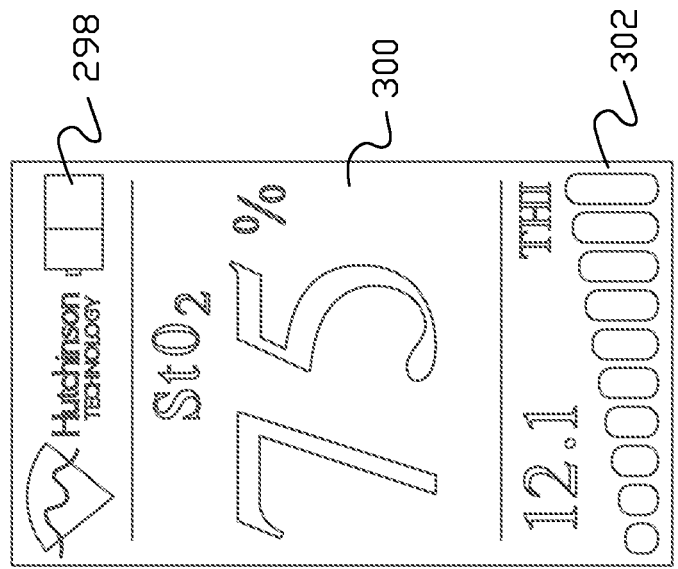

FIGS. 31A-31G represent several example display screens during normal device operation. FIG. 31A shows, for example, a load-up indicator 296 that can be seen on the display immediately on start-up of the monitor. FIG. 31B shows a screen that can be displayed before any action has been taken by the user, and which as shown, includes a battery status indicator 298, an StO$_2$ level indicator 300, and a THI level indicator 302.

Figure 31C:
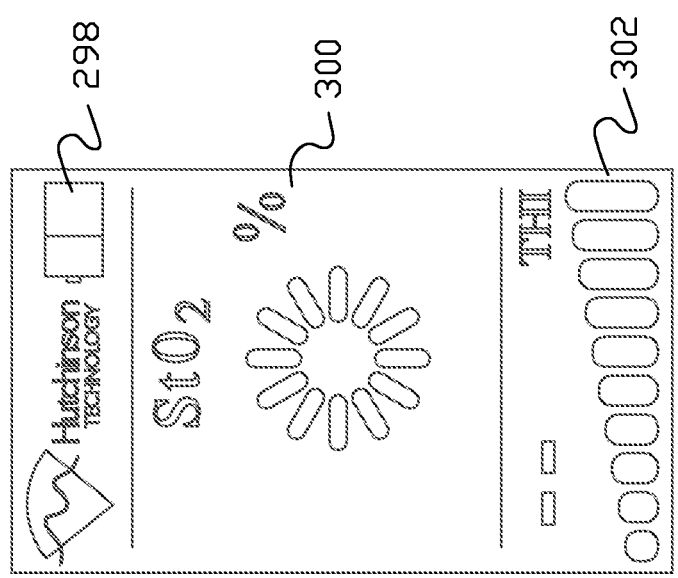

FIG. 31C shows an example screen that can be displayed on the display when an StO$_2$ reading is in progress. Once a reading is obtained, and as further shown in FIG. 31D, a number (e.g., "75%") can be displayed for the StO$_2$ level indicator 300 along with a value (e.g., "12.1") for the THI level indicator 302 calculated by the monitor. FIG. 31E shows an example screen that can be displayed when there is a low battery event. FIG. 31F, in turn, shows an example screen that can be displayed when the on/off switch has been depressed and the monitor is shutting down. FIG. 31G shows an example screen that can be displayed in the event the monitor experiences an error. A sample error message can be displayed, for example, in the event the connection of the patient interface to the patient is insufficient or when the electro-optical connector is not fully connected. Other display messages and/or screens are also possible.

FIGS. 31H-31J represent several example display screens that can be displayed during a system check. In some embodiments, for example, FIGS. 31H-31J may represent several illustrative screens that can be displayed in response to selecting the system check button 38 on monitor 30. As shown in a first display screen in FIG. 31H, a status indicator 304 can be provided on the display indicating that a system check is currently being performed. Other information such as the expected ranges for the StO$_2$ and THI levels can also be displayed, as shown.

FIG. 31I shows an example display screen that can be displayed in the event the system check passes. The screen can include the tested StO$_2$ and THI readout levels (e.g., 52% StO2 and 9.1 THI) along with expected range levels. The readout levels can be presented in a first color (e.g., green) to indicate that the system check passed. FIG. 31J, in turn, shows an example display screen that can be provided in the event the system fails a system check. As can be seen in FIG. 31J, the readout (e.g., 43% and 7.2 THI) falls outside of the desired ranges. To indicate this, the readout levels can also be displayed in a color (e.g., red) indicative of a failed test.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A patient interface for a tissue measurement instrument, the patient interface comprising:
   a spring clip including a first arm member and a second arm member, the first and second arm members configured to provide a clamping force on a measurement site of a patient;
   a pressure dispersion pad coupled to at least one of the first and second arm members, the pressure dispersion pad comprising an opaque pressure dispersion pad configured to shield light from the measurement site;
   a plurality of radiation ports disposed in one or both of the first and second arm members, the radiation ports configured for light transmission therethrough;
   a spring configured to bias the first and second arm members together; and
   a means for optically connecting the patient interface to the tissue measurement instrument,
   wherein the first and second arm members and the spring comprise a single member.

2. The patient interface of claim 1, wherein the spring includes a plurality of bending spring elements.

3. The patient interface of claim 2, wherein the spring elements are zigzags.

4. The patient interface of claim 1, wherein the pressure dispersion pad is a cup-shaped pad.

5. The patient interface of claim 1, wherein the pressure dispersion pad is a gimballing pressure pad.

6. The patient interface of claim 1, wherein the pressure dispersion pad includes a number of locating features configured to align the patient interface to the measurement site on the patient.

7. The patient interface of claim 1, wherein the radiation ports comprise a first radiation port configured for transmitting light and a second radiation port configured for receiving reflected light.

8. The patient interface of claim 1, further including a light shield coupled to at least one of the first and second arm members, the light shield including a number of shield radiation ports in optical communication with the radiation ports.

9. A patient interface for a tissue measurement instrument, the patient interface comprising:
   a spring clip including a first arm member and a second arm member, the first and second arm members configured to provide a clamping force on a measurement site of a patient, the first and second arm members comprise separate members releasably coupled to each other;
   a plurality of radiation ports disposed in one or both of the first and second arm members, the radiation ports configured for light transmission therethrough;
   a spring configured to bias the first and second arm members together; and
   an optical connector optically connecting the patient interface to the tissue measurement instrument,
   wherein the second arm member and the spring comprise a single member separate from the first arm member.

10. The patient interface of claim 9, wherein the first and second arm members are pivotally coupled to each other.

11. The patient interface of claim 9, further including a release button configured for engaging a tab that secures the first arm member to the second arm member.

12. The patient interface of claim 9, wherein the spring includes a plurality of bending spring elements.

13. The patient interface of claim 12, wherein the spring elements are zigzags.

14. The patient interface of claim 9, further including a pressure dispersion pad coupled to at least one of the first and second arm members, wherein the pressure dispersion pad is configured to one or both of gimbal and shield light from the measurement site.

15. A patient interface for a tissue measurement instrument, the patient interface comprising:
   a spring clip including a first arm member and a second arm member, the first and second arm members configured to provide a clamping force on a measurement site of a patient;
   a plurality of radiation ports disposed in one or both of the first and second arm members, the radiation ports configured for light transmission therethrough;
   a spring configured to bias the first and second arm members together; and
   an optical connector optically connecting the patient interface to the tissue measurement instrument,
   wherein the first and second arm members comprise separate members releasably coupled to each other.

16. The patient interface of claim 15, further including a release button configured for engaging a tab that secures the first arm member to the second arm member.

17. A patient interface for a tissue measurement instrument, the patient interface comprising:
   a spring clip including a first arm member and a second arm member, the first and second arm members configured to provide a clamping force on a measurement site of a patient;
   a plurality of radiation ports disposed in one or both of the first and second arm members, the radiation ports configured for light transmission therethrough;
   a spring configured to bias the first and second arm members together;
   an optical connector optically connecting the patient interface to the tissue measurement instrument; and
   a gimballing pressure dispersion pad coupled to at least one of the first and second arm members.

18. The patient interface of claim 17, wherein the pressure dispersion pad is a cup-shaped pad.

19. The patient interface of claim 17, wherein the pressure dispersion pad includes a number of locating features configured to align the patient interface to the measurement site on the patient.

20. A patient interface for a tissue measurement instrument, the patient interface comprising:
   a spring clip including a first arm member and a second arm member, the first and second arm members configured to provide a clamping force on a measurement site of a patient;
   a plurality of radiation ports disposed in one or both of the first and second arm members, the radiation ports configured for light transmission therethrough;
   a spring configured to bias the first and second arm members together;
   an optical connector optically connecting the patient interface to the tissue measurement instrument; and
   a pressure dispersion pad coupled to at least one of the first and second arm members, the pressure dispersion pad comprising an opaque pressure dispersion pad configured to shield light from the measurement site, wherein the pressure dispersion pad is a gimballing pressure pad.

21. The patient interface of claim 20, wherein the pressure dispersion pad is a cup-shaped pad.

22. The patient interface of claim 20, wherein the pressure dispersion pad includes a number of locating features configured to align the patient interface to the measurement site on the patient.

23. A patient interface for a tissue measurement instrument, the patient interface comprising:
- a spring clip including a first arm member and a second arm member, the first and second arm members configured to provide a clamping force on a measurement site of a patient;
- a pressure dispersion pad coupled to at least one of the first and second arm members, wherein the pressure dispersion pad is a gimballing pressure pad;
- a plurality of radiation ports disposed in one or both of the first and second arm members, the radiation ports configured for light transmission therethrough;
- a spring configured to bias the first and second arm members together; and
- a means for optically connecting the patient interface to the tissue measurement instrument,
wherein the first and second arm members and the spring comprise a single member.

24. A patient interface for a tissue measurement instrument, the patient interface comprising:
- a spring clip including a first arm member and a second arm member, the first and second arm members configured to provide a clamping force on a measurement site of a patient;
- a pressure dispersion pad coupled to at least one of the first and second arm members, wherein the pressure dispersion pad is configured to one or both of gimbal and shield light from the measurement site;
- a plurality of radiation ports disposed in one or both of the first and second arm members, the radiation ports configured for light transmission therethrough;
- a spring configured to bias the first and second arm members together; and
- an optical connector optically connecting the patient interface to the tissue measurement instrument,
wherein the second arm member and the spring comprise a single member separate from the first arm member.

* * * * *